(12) United States Patent
Hakamata

(10) Patent No.: US 6,226,089 B1
(45) Date of Patent: *May 1, 2001

(54) METHOD OF AND SYSTEM FOR MEASURING GLUCOSE CONCENTRATION

(75) Inventor: Kazuo Hakamata, Kanagawa-ken (JP)

(73) Assignee: Fuji Photo Film Co., LTD, Kanagawa-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/359,642

(22) Filed: Jul. 26, 1999

(30) Foreign Application Priority Data

Jul. 24, 1998 (JP) .................................. 10-209118

(51) Int. Cl.[7] .................................................. G01N 21/00
(52) U.S. Cl. ........................................... 356/432; 600/319
(58) Field of Search .............................. 356/432; 600/319

(56) References Cited

U.S. PATENT DOCUMENTS

| 3,958,560 | 5/1976 | March | 128/2 A |
|---|---|---|---|
| 5,243,983 | 9/1993 | Tarr et al. | 128/633 |
| 5,535,743 | 7/1996 | Backhaus et al. | 128/633 |
| 5,553,617 | * 9/1996 | Barkenhagen | 128/633 |
| 5,666,956 | * 9/1997 | Buchert | 128/664 |
| 5,835,215 | 11/1998 | Toida et al. | 356/349 |
| 5,885,224 | * 3/1999 | Yoshida | 600/558 |
| 6,152,875 | * 11/2000 | Hakamata | 600/319 |

FOREIGN PATENT DOCUMENTS 0 859 410 A2   8/1998   (EP) ............................ H01L/23/373

* cited by examiner

Primary Examiner—Frank G. Font
Assistant Examiner—Phil Natividad
(74) Attorney, Agent, or Firm—Sughrue, Mion, Zinn, Macpeak & Seas, PLLC

(57) ABSTRACT

The intensities of backscattering light generated by predetermined interfaces of an eyeball when a laser beam emitted from a semiconductor laser is projected onto the eyeball in a predetermined position are detected. The absorbance or refractive index of the aqueous humor in the anterior chamber of the eyeball is determined on the basis of the intensities of the backscattering light, and the glucose concentration in the aqueous humor is determined on the basis of the absorbance or refractive index of the aqueous humor in the anterior chamber thus determined. An extinction filter is disposed on the optical path of the laser beam between the semiconductor laser and the eyeball so that the intensity of the laser beam entering the eyeball is reduced not higher than a predetermined value of MPE.

16 Claims, 9 Drawing Sheets

METHOD OF AND SYSTEM FOR MEASURING GLUCOSE CONCENTRATION

BACKGROUND OF THE INVENTION

1. Field of the Invention

This invention relates to a method of and a system for measuring the glucose concentration in an organism, and more particularly to a method of and a system for noninvasively measuring the glucose concentration in aqueous humor in an anterior chamber.

2. Description of the Related Art

Though the mean level of the glucose concentration in the blood varies from person to person, it is an important indication on the basis of which whether a diabetic is to be dosed is determined.

The blood glucose concentration largely varies in a very short time according to the kind of meal and/or physical activities or due to concurrence of diseases. An emergency dosing is often required due to abrupt increase of the blood glucose concentration.

Accordingly, it is desired that the blood glucose concentration of the patient be monitored at as short intervals as possible. Conventionally, the blood glucose concentration has been generally monitored by cutting the tip of a finger of the patient and analyzing the blood thus collected. Accordingly because of pain accompanying cutting the finger, it is difficult to force the patient to be subjected to measurement of the blood glucose concentration a plurality of times a day.

Recently there have been proposed noninvasive methods of measuring the blood glucose concentration instead of an invasive method having such drawback.

The noninvasive methods mainly involve noninvasive measurement of the glucose concentration in aqueous humor in the anterior chamber between the cornea and the lens of the human eyeball. The glucose concentration in aqueous humor in the anterior chamber has a close relation with the blood glucose concentration though the relation varies from person to person.

In one of such noninvasive methods, the glucose concentration is determined on the basis of optical rotation of infrared rays entering the aqueous humor in an anterior chamber as disclosed, for instance, in Japanese Unexamined Patent Publication No. 51(1976)-75498 (corresponding to U.S. Pat. No. 3,958,560). In another method, Raman scattering light by glucose is measured as disclosed, for instance, in PCT Japanese Publication No. 6(1994)-503245. In still another method, optical properties of light reflected by the lens is measured as disclosed, for instance, in Japanese Unexamined Patent Publication No. 6(1994)-237898.

We have proposed a noninvasive method of measuring the glucose concentration in aqueous humor in an anterior chamber in Japanese Unexamined Patent Publication No. 9(1997)-299333 in which a plurality of laser beams or the like different in wavelength band are caused to enter the eyeball, intensity of backscattering light from an interface between the cornea and the aqueous humor in the anterior chamber and intensity of backscattering light from an interface between the aqueous humor in the anterior chamber and the lens are accurately detected by wavelength band, for instance, by light heterodyne measurement, absorption properties of the aqueous humor for the respective wavelength bands are obtained on the basis of the backscattering light intensities and the like and the glucose concentration in the aqueous humor is obtained by near-infrared spectrometry including multivariate analysis on the basis of the absorption properties of the aqueous humor for the respective wavelength bands. Further we have proposed a noninvasive method of measuring the glucose concentration in aqueous humor in an anterior chamber in Japanese Patent Application No. 9(1997)-358101 in which the glucose concentration in the aqueous humor is determined on the basis of the refractive index of the aqueous humor in the anterior chamber which is determined on the basis of intensity or the like of reflected light from the anterior chamber, the refractive index of the aqueous humor in the anterior chamber having a very close relation with the glucose concentration in the aqueous humor.

In the systems where light is caused to enter the eyeball, it is necessary to suppress influence of the light on the eyeball as low as possible, and especially in the case where the light is a laser beam, the intensity of the laser beam must be carefully controlled.

However, in any of the above identified patent publications, there is no disclosure on a means for controlling the intensity of the laser beam to be entered in the eyeball.

SUMMARY OF THE INVENTION

In view of the foregoing observations and description, the primary object of the present invention is to provide a method of and a system for measuring the glucose concentration in aqueous humor in an anterior chamber in which the intensity of a laser beam to be entered in the eyeball can be properly controlled.

In accordance with a first aspect of the present invention, there is provided a method of measuring the glucose concentration in aqueous humor in an anterior chamber comprising the steps of detecting the intensities of backscattering light generated by predetermined interfaces of an eyeball when a laser beam emitted from a semiconductor laser is projected onto the eyeball in a predetermined position, determining the absorbance or refractive index of the aqueous humor in the anterior chamber of the eyeball on the basis of the intensities of the backscattering light, and determining the glucose concentration in the aqueous humor on the basis of the absorbance or refractive index of the aqueous humor in the anterior chamber thus determined, wherein the improvement comprises the steps of disposing an extinction filter on the optical path of the laser beam between the semiconductor laser and the eyeball so that the intensity of the laser beam entering the eyeball is reduced not higher than a predetermined value of MPE.

The MPE is a maximum permissible exposure (JIS C 6801, 6802) defined in JIS (Japanese Industrial Standard) and applied to exposure of the eyeball to a laser beam.

The predetermined value of MPE is obtained on the basis of the following tables 1 and 2 which are an extract of JIS C 6802 "Table 2, MPE values for eyes watching a divergent light source". For example, when the eyeball is to be exposed using the optical system shown in FIG. 10 to a laser beam of a wavelength of 700 nm to 1050 nm for one second with a solid angle of $3.5\times10^{-4}$ and a beam size of 0.038 $mm^{-2}$ at the surface of the eyeball, the predetermined value of MPE is 10 $\mu W$, and when the eyeball is to be exposed using the optical system shown in FIG. 10 to a laser beam of a wavelength of 1050 nm to 1400 nm for one second with a solid angle of $3.5\times10^{-4}$ and a beam size of 0.038 $mm^{-2}$ at the surface of the eyeball, the predetermined value of MPE is 40 $\mu W$.

TABLE 1

| wavelength[nm] | exposure time $10^{-8}$ to 10 [seconds] |
| --- | --- |
| 700 to 1050 | $10^5 \times 10^{\{(\lambda-700)/500\}} \times t^{0.33}$ [Jm$^{-2}$sr$^{-1}$] |
| 1050 to 1400 | $5 \times 10^5 \times t^{0.33}$ [Jm$^{-2}$sr$^{-1}$] |

TABLE 2

| wavelength[nm] | exposure time $10^3$ to $3 \times 10^4$ [seconds] |
| --- | --- |
| 700 to 1050 | $6.4 \times 10^3 \times 10^{\{(\lambda-700)/500\}}$ [Wm$^{-2}$sr$^{-1}$] |
| 1050 to 1400 | $3.2 \times 10^4$ [Wm$^{-2}$sr$^{-1}$] |

As the correlation of the refractive index of aqueous humor in an anterior chamber and the glucose concentration therein, for instance, that shown in FIG. 6 may be employed. The correlation shown in FIG. 6 can be typically expressed by the following regression equation (correlation coefficient:0.9516).

$$n_2 = 1.33322 + 1.6 \times 10^{-6} \times G$$

wherein G represents the glucose concentration (mg/dl).

For example, the semiconductor laser may radiate a laser beam in a visible region or a near-infrared region at an intensity of several mW (1 to 9 mW, e.g., 3 to 4 mW) and a ND filter whose optical density is in the range of 3 to 4 inclusive may be employed as the extinction filter.

The absorbance of the aqueous humor in the anterior chamber of the eyeball is determined on the basis of the intensities of the backscattering light from an interface between the cornea and the aqueous humor in the anterior chamber and an interface between the aqueous humor in the anterior chamber and the lens. The refractive index of the aqueous humor in the anterior chamber of the eyeball is determined on the basis of the intensities of the backscattering light from an interface between air and the cornea and an interface between the cornea and the aqueous humor in the anterior chamber. That is, when the glucose concentration in the aqueous humor is to be determined on the basis of the absorbance, said predetermined interfaces are an interface between air and the cornea and an interface between the cornea and the aqueous humor in the anterior chamber, and when the glucose concentration in the aqueous humor is to be determined on the basis of the refractive index of the aqueous humor in the anterior chamber, then said predetermined interfaces are an interface between air and the cornea and an interface between the cornea and the aqueous humor in the anterior chamber.

It is preferred that the glucose concentration in the aqueous humor in an anterior chamber be determined on the basis of the absorbance of the aqueous humor in accordance with one of the following methods (A1) to (A3).

(A1) A laser beam of low coherence emitted from a semiconductor laser is divided into two parts, a signal light beam and a reference light beam, which travel along two different optical paths. At least one of the signal light beam and the reference light beam is modulated in such a way that a slight frequency difference is produced between them. The signal light beam is projected onto an eyeball which has been in a predetermined position, and first backscattering light of the signal light beam generated by the interface between the cornea and the aqueous humor is caused to interfere with the reference light beam by controlling the length of the optical path of the reference light beam. The intensity of first interference light obtained by the interference between the first backscattering light and the reference light beam is measured and the intensity of the first backscattering light is determined on the basis of the intensity of the first interference light.

Then second backscattering light of the signal light beam generated by the interface between the aqueous humor and the lens is caused to interfere with the reference light beam by controlling the length of the optical path of the reference light beam. The intensity of second interference light obtained by the interference between the second backscattering light and the reference light beam is measured and the intensity of the second backscattering light is determined on the basis of the intensity of the second interference light.

The absorbance of the aqueous humor in the anterior chamber to the laser beam is determined on the basis of the intensities of the first and second backscattering light.

The absorbances of the aqueous humor in the anterior chamber to a plurality of laser beams which are different from the laser beam in wavelength band are determined in the similar manner. Then the glucose concentration in the aqueous humor is determined on the basis of the absorbances of the aqueous humor to the laser beams.

The semiconductor laser is preferably a super luminescent diode which emits a laser beam which is short (about several tens $\mu$m) in distance of interference and is highly directive.

To measure the intensity of the interference light is to measure the intensity of a beat signal (interference light) which beats at the frequency difference between the backscattering light (signal light beam) and the reference light beam.

In the method of A1, the laser beams of low coherence may be extracted from light having a wider wavelength band or may be separately emitted from different light sources.

In the case where the laser beams are emitted from a plurality of semiconductor lasers, the lasers are caused in sequence to emit low coherent laser beams in different wavelength bands and the backscattering light for the respective laser beams is detected by a single photodetector.

(A2) A coherent laser beam which is emitted from a semiconductor laser and is frequency-swept with time in a saw tooth shape (e.g., as shown in FIG. 8) is divided into a signal light beam and a reference light beam which travel along two different optical paths. The signal light beam is projected onto an eyeball which has been in a predetermined position, and first backscattering light of the signal light beam generated by the interface between the cornea and the aqueous humor is caused to interfere with the coherent reference light beam which is different from the first backscattering light in frequency and is emitted from the semiconductor laser with a time difference based on the difference between the length of the optical path of the signal light beam (between the point at which the signal light beam is separated from the reference light beam and the interface between the cornea and the aqueous humor) and the first backscattering light (between the interface between the cornea and the aqueous humor and the point at which the first backscattering light interferes with the reference light beam) and the length of the optical path of the reference light beam (between the point at which the reference light beam is separated from the signal light beam and the point at which the first backscattering light interferes with the reference light beam). The intensity of first interference light obtained by the interference between the first backscattering light and the reference light beam is measured and the intensity of the first backscattering light is determined on the basis of the intensity of the first interference light.

Then second backscattering light of the signal light beam generated by the interface between the aqueous humor and the lens is caused to interfere with the coherent reference light beam which is different from the second backscattering light in frequency and is emitted from the semiconductor laser with a time difference based on the difference between the length of the optical path of the signal light beam (between the point at which the signal light beam is separated from the reference light beam and the interface between the aqueous humor and the lens) and the second backscattering light (between the interface between the aqueous humor and the lens and the point at which the second backscattering light interferes with the reference light beam) and the length of the optical path of the reference light beam (between the point at which the reference light beam is separated from the signal light beam and the point at which the second backscattering light interferes with the reference light beam). The intensity of second interference light obtained by the interference between the second backscattering light and the reference light beam is measured and the intensity of the second backscattering light is determined on the basis of the intensity of the second interference light.

The absorbance of the aqueous humor in the anterior chamber to said laser beam is determined on the basis of the intensities of the first and second backscattering light.

The absorbances of the aqueous humor in the anterior chamber to a plurality of coherent laser beams which are different from said coherent laser beam in wavelength are determined in the similar manner. Then the glucose concentration in the aqueous humor is determined on the basis of the absorbances of the aqueous humor to the coherent laser beams.

In the method of A2, the coherent laser beams may be selectively emitted from a single semiconductor laser or may be separately emitted from different semiconductor lasers.

(A3) A laser beam emitted from a semiconductor laser in the form of ultrashort pulse light is projected onto an eyeball and intensities of first backscattering light of the laser beam generated by the interface between the cornea and the aqueous humor and second backscattering light of the laser beam generated by the interface between the aqueous humor and the lens are separately measured. The absorbance of the aqueous humor in the anterior chamber to said laser beam is determined on the basis of the intensities of the first and second backscattering light.

The absorbances of the aqueous humor in the anterior chamber to a plurality of laser beams in the form of ultrashort pulse light which are different from said laser beam in wavelength are determined in the similar manner. Then the glucose concentration in the aqueous humor is determined on the basis of the absorbances of the aqueous humor to the laser beams.

The ultrashort pulse light is a light pulse which is emitted for such a very short time (e.g., femtoseconds to picoseconds) that the intensities of the first and second backscattering light can be measured separated by time from each other. When such ultrashort pulse light is employed, the second backscattering light delays after the first backscattering light by the time required for the second backscattering light to travel back and forth across the anterior chamber and can be detected separately from the first backscattering light by a photodetector such as a streak camera which is capable of time resolving.

Also in the method of A3, the ultrashort pulse laser beams may be selectively emitted from a single semiconductor laser or may be separately emitted from different semiconductor lasers.

The glucose concentration in the aqueous humor in an anterior chamber can be determined on the basis of the refractive index of the aqueous humor in accordance with, for instance, one of the following methods (B1) to (B4).

(B1) A laser beam of low coherence emitted from a semiconductor laser is divided into a signal light beam and a reference light beam which travel along two different optical paths. At least one of the signal light beam and the reference light beam is modulated in such a way that a slight frequency difference is produced between them. The signal light beam is projected onto an eyeball which has been in a predetermined position, and first backscattering light of the signal light beam generated by the interface between air and the cornea is caused to interfere with the reference light beam by controlling the length of the optical path of the reference light beam. The intensity of first interference light obtained by the interference between the first backscattering light and the reference light beam is measured and the intensity of the first backscattering light is determined on the basis of the intensity of the first interference light.

Then second backscattering light of the signal light beam generated by the interface between the cornea and the aqueous humor is caused to interfere with the reference light beam by controlling the length of the optical path of the reference light beam. The intensity of second interference light obtained by the interference between the second backscattering light and the reference light beam is measured and the intensity of the second backscattering light is determined on the basis of the intensity of the second interference light.

The refractive index of the aqueous humor in the anterior chamber is determined on the basis of the intensities of the first and second backscattering light.

Then the glucose concentration in the aqueous humor is determined on the basis of the refractive index of the aqueous humor thus determined and according to a correlation between the refractive index of the aqueous humor and the glucose concentration therein which has been obtained in advance.

The semiconductor laser is preferably a super luminescent diode which emits a laser beam which is short (about several tens $\mu$m) in distance of interference and is highly directive.

(B2) A coherent laser beam which is emitted from a semiconductor laser and is frequency-swept with time in a saw tooth shape is divided into a signal light beam and a reference light beam which travel along two different optical paths. The signal light beam is projected onto an eyeball which has been in a predetermined position, and first backscattering light of the signal light beam generated by the interface between air and the cornea is caused to interfere with the coherent reference light beam which is different from the first backscattering light in frequency and is emitted from the semiconductor laser with a time difference based on the difference between the length of the optical path of the signal light beam (between the point at which the signal light beam is separated from the reference light beam and the interface between air and the cornea) and the first backscattering light (between the interface between air and the cornea and the point at which the first backscattering light interferes with the reference light beam) and the length of the optical path of the reference light beam (between the point at which the reference light beam is separated from the signal light beam and the point at which the first backscattering light interferes with the reference light beam). The intensity of first interference light obtained by the interference between the first backscattering light and the reference light beam is measured and the intensity of the first backscattering light is determined on the basis of the intensity of the first interference light.

Then second backscattering light of the signal light beam generated by the interface between the aqueous humor and the cornea is caused to interfere with the coherent reference light beam which is different from the second backscattering light in frequency and is emitted from the semiconductor laser with a time difference based on the difference between the length of the optical path of the signal light beam (between the point at which the signal light beam is separated from the reference light beam and the interface between the aqueous humor and the cornea) and the second backscattering light (between the interface between the aqueous humor and the cornea and the point at which the second backscattering light interferes with the reference light beam) and the length of the optical path of the reference light beam (between the point at which the reference light beam is separated from the signal light beam and the point at which the second backscattering light interferes with the reference light beam). The intensity of second interference light obtained by the interference between the second backscattering light and the reference light beam is measured and the intensity of the second backscattering light is determined on the basis of the intensity of the second interference light.

The refractive index of the aqueous humor in the anterior chamber is determined on the basis of the intensities of the first and second backscattering light.

Then the glucose concentration in the aqueous humor is determined on the basis of the refractive index of the aqueous humor thus determined and according to a correrlation between the refractive index of the aqueous humor and the glucose concentration therein which has been obtained in advance.

(B3) A laser beam emitted from a semiconductor laser in the form of ultrashort pulse light is projected onto an eyeball and intensities of first backscattering light of the laser beam generated by the interface between the cornea and air and second backscattering light of the laser beam generated by the interface between the aqueous humor and the cornea are separately measured. The refractive index of the aqueous humor in the anterior chamber is determined on the basis of the intensities of the first and second backscattering light.

Then the glucose concentration in the aqueous humor is determined on the basis of the refractive index of the aqueous humor thus determined and according to a correrlation between the refractive index of the aqueous humor and the glucose concentration therein which has been obtained in advance.

The ultrashort pulse light is a light pulse which is emitted for such a very short time (e.g., femtoseconds to picoseconds) that the intensities of the first and second backscattering light can be measured separated by time from each other. When such ultrashort pulse light is employed, the second backscattering light delays after the first backscattering light by the time required for the second backscattering light to travel back and forth across the anterior chamber and can be detected separately from the first backscattering light by a photodetector such as a streak camera which is capable of time resolving.

(B4) A laser beam emitted from a semiconductor laser is projected onto an eyeball which has been in a predetermined position and intensities of first backscattering light of the laser beam generated by the interface between the cornea and air and second backscattering light of the laser beam generated by the interface between the aqueous humor and the cornea are separately measured by use of a confocal optical system, having one focal point on each of the interfaces and a pin hole disposed on the other focal point, in a position conjugate to each interface. The refractive index of the aqueous humor in the anterior chamber is determined on the basis of the intensities of the first and second backscattering light.

Then the glucose concentration in the aqueous humor is determined on the basis of the refractive index of the aqueous humor thus determined and according to a correrlation between the refractive index of the aqueous humor and the glucose concentration therein which has been obtained in advance.

The intensity of each of the first and second backscattering light can be detected by use of a confocal optical system in a position conjugate to the corresponding interface by disposing the pin hole in a position conjugate to the corresponding interface so that only the backscattering light focused at the pin hole can pass through the pin hole and detecting the light passing through the pin hole. By moving the pin hole or at least one element of the optical system in the direction of the optical axis of the optical system, one of the first and second backscattering light can be selectively detected.

In accordance with a second aspect of the present invention, there is provided a method of measuring the glucose concentration in aqueous humor in an anterior chamber comprising the steps of detecting the state of elliptical polarization of backscattering light generated by a predetermined interface of an eyeball when a laser beam emitted from a semiconductor laser is projected onto the eyeball in a predetermined position, determining the refractive index of the aqueous humor in the anterior chamber of the eyeball on the basis of the state of elliptical polarization of the backscattering light, and determining the glucose concentration in the aqueous humor on the basis of the refractive index of the aqueous humor in the anterior chamber thus determined, wherein the improvement comprises the steps of disposing an extinction filter on the optical path of the laser beam between the semiconductor laser and the eyeball so that the intensity of the laser beam entering the eyeball is reduced not higher than a predetermined value of MPE.

Determining the refractive index of the aqueous humor in the anterior chamber of the eyeball on the basis of the state of elliptical polarization of the backscattering light, and determining the glucose concentration in the aqueous humor on the basis of the refractive index of the aqueous humor in the anterior chamber thus determined can be effected, for instance, in the following manner. A circularly polarized laser beam is caused to impinge upon the eyeball at a predetermined incident angle and the state of elliptical polarization of the backscattering light of the laser beam generated by the interface between the aqueous humor and the cornea is measured by use of a confocal optical system in a position conjugate to the interface. The refractive index of the aqueous humor in the anterior chamber is determined on the basis of the state of elliptical polarization of the backscattering light. Then the glucose concentration in the aqueous humor is determined on the basis of the refractive index of the aqueous humor thus determined and according to a correrlation between the refractive index of the aqueous humor and the glucose concentration therein which has been obtained in advance.

The backscattering light can be detected by use of a confocal optixal system in a position conjugate to the corresponding interface by disposing the pin hole in a position cojugate to the corresponding interface so that only the backscattering light focused at the pin hole can pass through the pin hole and detecting the light passing through the pin hole.

Specifically, the refractive index of the aqueous humor in the anterior chamber can be determined on the basis of the state of elliptical polarization of the backscattering light by use of the principle of ellipsometer. That is, an amplitude ratio $\psi$ and a phase difference $\Delta$ are obtained from the ellipticity $\rho$ and the azimuth $\phi$ of elliptical polarization of the backscattering light obtained by the measurement and the refractive index n of the aqueous humor is given by the following formula wherein $\psi_0$ represents the angle of incidence to the eyeball which is known.

$$n^2 = \sin^2 \psi_0 [1 + \{\tan^2 \psi_0 (\cos^2 2\psi - \sin^2 2\psi \sin^2 \Delta)\}/(1 + \sin 2\psi \cos \Delta)^2]$$

In accordance with a third aspect of the present invention, there is provided a glucose concentration measuring system for carrying out the method in accordance with the first aspect in which the intensities of backscattering light generated by predetermined interfaces of an eyeball when a laser beam emitted from a semiconductor laser is projected onto the eyeball in a predetermined position are detected, the absorbance or refractive index of the aqueous humor in the anterior chamber of the eyeball is determined on the basis of the intensities of the backscattering light, and the glucose concentration in the aqueous humor is determined on the basis of the absorbance or refractive index of the aqueous humor in the anterior chamber thus determined, wherein the improvement comprises an extinction filter disposed on the optical path of the laser beam between the semiconductor laser and the eyeball so that the intensity of the laser beam entering the eyeball is reduced not higher than a predetermined value of MPE.

For example, the semiconductor laser may radiate a laser beam in a visible region or a near-infrared region at an intensity of several mW (1 to 9 mW, e.g., 3 to 4 mW) and a ND filter whose optical density is in the range of 3 to 4 inclusive may be employed as the extinction filter.

It is preferred that the glucose concentration in the aqueous humor in an anterior chamber be determined on the basis of the absorbance of the aqueous humor by use of one of the following systems (A1') to (A3').

(A1') A system comprising a semiconductor laser which emits a plurality of laser beams which are of low coherence and are different from each other in wavelength band, a beam splitter means which divides each of the laser beams emitted from the semiconductor laser into a signal light beam and a reference light beam travelling along two different optical paths so that the signal light beam impinges upon the eyeball, a light modulator means which modulates at least one of the signal light beam and the reference light beam in such a way that a slight frequency difference is produced between them, an optical length controlling means for controlling the length of the optical path of the reference light beam, a wavefront matching means which brings each of first backscattering light of the signal light beam generated by the interface between the cornea and the aqueous humor and second backscattering light of the signal light beam generated by the interface between the aqueous humor and the lens into wavefront matching with the reference light beam, a photodetector which photoelectrically detects the intensity of first interference light obtained by the wavefront matching between the first backscattering light and the reference light beam and the intensity of second interference light obtained by the wavefront matching between the second backscattering light and the reference light beam, a heterodyne operation means which determines the intensities of the first and second backscattering light on the basis of the intensities of the first and second interference light, an absorption analysis means which determines absorption properties of the aqueous humor in the anterior chamber on the basis of the intensities of the first and second backscattering light, and a glucose concentration calculating means which obtains the glucose concentration in the aqueous humor on the basis of the absorption properties of the aqueous humor to said plurality of laser beams.

The semiconductor laser may comprise a single semiconductor laser which emits light of low coherence having a wider wavelength band than each of said laser beams of low coherence and a wavelength selector which extracts each of said laser beam from the light by wavelength selection or may comprise a plurality of semiconductor lasers which emit said laser beams respectively.

(A2') A system comprising a semiconductor laser which emits a plurality of coherent laser beams which are different from each other in wavelength band and are frequency-swept with time in a saw tooth shape (e.g., as shown in FIG. 8), a beam splitter means which divides each of the laser beams emitted from the semiconductor laser into a signal light beam and a reference light beam travelling along two different optical paths so that the signal light beam impinges upon the eyeball, a wavefront matching means which brings first backscattering light of the signal light beam generated by the interface between the cornea and the aqueous humor into wavefront matching with the coherent reference light beam which is different from the first backscattering light in frequency and is emitted from the semiconductor laser with a time difference based on the difference between the length of the optical path of the signal light beam and the first backscattering light and the length of the optical path of the reference light beam and brings second backscattering light of the signal light beam generated by the interface between the aqueous humor and the lens into wavefront matching with the coherent reference light beam which is different from the second backscattering light in frequency and is emitted from the semiconductor laser with a time difference based on the difference between the length of the optical path of the signal light beam and the second backscattering light and the length of the optical path of the reference light beam, a photodetector which photoelectrically detects the intensity of first interference light obtained by the wavefront matching between the first backscattering light and the reference light beam having a slight frequency difference relative to the first backscattering light and the intensity of second interference light obtained by the wavefront matching between the second backscattering light and the reference light beam having a slight frequency difference relative to the first backscattering light, a heterodyne operation means which determines the intensities of the first and second backscattering light on the basis of the intensities of the first and second interference light, an absorption analysis means which determines absorption properties of the aqueous humor in the anterior chamber on the basis of the intensities of the first and second backscattering light, and a glucose concentration calculating means which obtains the glucose concentration in the aqueous humor on the basis of the absorption properties of the aqueous humor to said plurality of coherent laser beams.

Also in this system, the semiconductor laser may comprise a single semiconductor laser which emits light of low coherence having a wider wavelength band than each of said laser beams of low coherence and a wavelength selector which extracts each of said laser beam from the light by wavelength selection or may comprise a plurality of semiconductor lasers which emit said laser beams respectively.

(A3') A system comprising a semiconductor laser which emits a plurality of laser beams which are in the form of ultrashort pulse light and are different from each other in wavelength, a backscattering light measuring means which causes the laser beams to enter the eyeball and separately measures in time series intensities of first backscattering light of the laser beam generated by the interface between the cornea and the aqueous humor and second backscattering light of the laser beam generated by the interface between the aqueous humor and the lens, an absorption analysis means which determines absorption properties of the aqueous humor in the anterior chamber on the basis of the intensities of the first and second backscattering light, and a glucose concentration calculating means which obtains the glucose concentration in the aqueous humor on the basis of the absorption properties of the aqueous humor to said plurality of ultrashort pulse laser beams.

The semiconductor laser may comprise a single semiconductor laser which selectively emits said plurality of ultrashort pulse laser beams and a control means which controls the semiconductor laser to selectively emit one of the laser beams or may comprise a plurality of semiconductor lasers which emit said laser beams respectively.

It is preferred that the glucose concentration in the aqueous humor in an anterior chamber be determined on the basis of the refractive index of the aqueous humor by use of one of the following systems (B1') to (B4').

(B1') A system comprising a semiconductor laser which emits a laser beam of low coherence, a beam splitter means which divides the laser beam emitted from the semiconductor laser into a signal light beam and a reference light beam travelling along two different optical paths so that the signal light beam impinges upon the eyeball, a light modulator means which modulates at least one of the signal light beam and the reference light beam in such a way that a slight frequency difference is produced between them, an optical length controlling means for controlling the length of the optical path of the reference light beam, a wavefront matching means which brings each of first backscattering light of the signal light beam generated by the interface between the cornea and air and second backscattering light of the signal light beam generated by the interface between the aqueous humor and the cornea into wavefront matching with the reference light beam, a photodetector which photoelectrically detects the intensity of first interference light obtained by the wavefront matching between the first backscattering light and the reference light beam and the intensity of second interference light obtained by the wavefront matching between the second backscattering light and the reference light beam, a heterodyne operation means which determines the intensities of the first and second backscattering light on the basis of the intensities of the first and second interference light, a refractive index calculating means which determines the refractive index of the aqueous humor in the anterior chamber on the basis of the intensities of the first and second backscattering light, a memory which stores a correlation between the refractive index of the aqueous humor and the glucose concentration therein which has been obtained in advance, and a glucose concentration calculating means which obtains the glucose concentration in the aqueous humor on the basis of the refractive index of the aqueous humor determined by the refractive index calculating means and according to the correlation between the refractive index of the aqueous humor and the glucose concentration therein stored in the memory.

(B2') A system comprising a semiconductor laser which emits a coherent laser beam which is frequency-swept with time in a saw tooth shape, a beam splitter means which divides the coherent laser beam emitted from the semiconductor laser into a signal light beam and a reference light beam travelling along two different optical paths so that the signal light beam impinges upon the eyeball, a wavefront matching means which brings first backscattering light of the signal light beam generated by the interface between the cornea and air into wavefront matching with the coherent reference light beam which is different from the first backscattering light in frequency and is emitted from the semiconductor laser with a time difference based on the difference between the length of the optical path of the signal light beam and the first backscattering light and the length of the optical path of the reference light beam and brings second backscattering light of the signal light beam generated by the interface between the aqueous humor and the cornea into wavefront matching with the coherent reference light beam which is different from the second backscattering light in frequency and is emitted from the semiconductor laser with a time difference based on the difference between the length of the optical path of the signal light beam and the second backscattering light and the length of the optical path of the reference light beam, a photodetector which photoelectrically detects the intensity of first interference light obtained by the wavefront matching between the first backscattering light and the reference light beam having a slight frequency difference relative to the first backscattering light and the intensity of second interference light obtained by the wavefront matching between the second backscattering light and the reference light beam having a slight frequency difference relative to the first backscattering light, a heterodyne operation means which determines the intensities of the first and second backscattering light on the basis of the intensities of the first and second interference light, a refractive index calculating means which determines the refractive index of the aqueous humor in the anterior chamber on the basis of the intensities of the first and second backscattering light, a memory which stores a correlation between the refractive index of the aqueous humor and the glucose concentration therein which has been obtained in advance, and a glucose concentration calculating means which obtains the glucose concentration in the aqueous humor on the basis of the refractive index of the aqueous humor determined by the refractive index calculating means and according to the correlation between the refractive index of the aqueous humor and the glucose concentration therein stored in the memory.

(B3') A system comprising a semiconductor laser which emits a laser beam in the form of ultrashort pulse light, a backscattering light measuring means which causes the laser beam to enter the eyeball and separately measures in time series intensities of first backscattering light of the laser beam generated by the interface between the cornea and air and second backscattering light of the laser beam generated by the interface between the aqueous humor and the cornea, a refractive index calculating means which determines the refractive index of the aqueous humor in the anterior chamber on the basis of the intensities of the first and second backscattering light, a memory which stores a correlation between the refractive index of the aqueous humor and the glucose concentration therein which has been obtained in advance, and a glucose concentration calculating means which obtains the glucose concentration in the aqueous humor on the basis of the refractive index of the aqueous humor determined by the refractive index calculating means and according to the correlation between the refractive index of the aqueous humor and the glucose concentration therein stored in the memory.

(B4') A system comprising a semiconductor laser which projects a laser beam onto an eyeball which has been in a predetermined position, a confocal optical system which spatially separates first backscattering light of the laser beam generated by the interface between the cornea and air and second backscattering light of the laser beam generated by the interface between the aqueous humor and the cornea from each other, the confocal optical system being capable of having one focal point on each of the interfaces with a pin hole disposed on the other focal point, a photodetector which photoelectrically detects the intensity of the first and second backscattering light spatially separated from each other by the confocal optical system, a refractive index calculating means which determines the refractive index of the aqueous humor in the anterior chamber on the basis of the intensities of the first and second backscattering light, a memory which stores a correlation between the refractive index of the aqueous humor and the glucose concentration therein which has been obtained in advance, and a glucose concentration calculating means which obtains the glucose concentration in the aqueous humor on the basis of the refractive index of the aqueous humor determined by the refractive index calculating means and according to the correlation between the refractive index of the aqueous humor and the glucose concentration therein stored in the memory.

In accordance with a fourth aspect of the present invention, there is provided a glucose concentration measuring system for carrying out the method in accordance with the second aspect in which the state of elliptical polarization of backscattering light generated by a predetermined interface of an eyeball when a laser beam emitted from a semiconductor laser is projected onto the eyeball in a predetermined position is detected, the refractive index of the aqueous humor in the anterior chamber of the eyeball is determined on the basis of the state of elliptical polarization of the backscattering light, and the glucose concentration in the aqueous humor is determined on the basis of the refractive index of the aqueous humor in the anterior chamber thus determined, wherein the improvement comprises an extinction filter disposed on the optical path of the laser beam between the semiconductor laser and the eyeball so that the intensity of the laser beam entering the eyeball is reduced not higher than a predetermined value of MPE.

Determining the refractive index of the aqueous humor in the anterior chamber of the eyeball on the basis of the state of elliptical polarization of the backscattering light, and determining the glucose concentration in the aqueous humor on the basis of the refractive index of the aqueous humor in the anterior chamber thus determined can be effected, for instance, by use of the following system. A system comprising a semiconductor laser which causes a circularly polarized laser beam to impinge upon the eyeball at a predetermined incident angle, a confocal optical system which extracts backscattering light of the laser beam generated by the interface between the aqueous humor and the cornea, an elliptical polarization detecting means which detects the state of elliptical polarization of the backscattering light extracted by the confocal optical system, a refractive index calculating means which determines the refractive index of the aqueous humor in the anterior chamber on the basis of the state of elliptical polarization of the backscattering light, a memory which stores a correlation between the refractive index of the aqueous humor and the glucose concentration therein which has been obtained in advance, and a glucose concentration calculating means which obtains the glucose concentration in the aqueous humor on the basis of the refractive index of the aqueous humor determined by the refractive index calculating means and according to the correlation between the refractive index of the aqueous humor and the glucose concentration therein stored in the memory.

The elliptical polarization detecting means may comprise, for instance, a polarizer such as a $\lambda/2$ plate which linearly polarizes the laser beam emitted from the semiconductor laser, a compensator plate such as a $\lambda/4$ plate which converts linearly polarized light to circularly polarized light, a reflecting mirror which reflects the circularly polarized light to impinge upon the eyeball as elliptically polarized light, and a combination of an analyzer and a photodetector which detect the azimuth and the amplitude of elliptically polarized light reflected from the eyeball.

In the method of and the system for measuring the glucose concentration in accordance with the present invention, an extinction filter disposed on the optical path of the laser beam between the semiconductor laser and the eyeball reduces the intensity of the laser beam entering the eyeball not higher than a predetermined value of MPE, thereby making harmless the laser beam.

Especially when the semiconductor laser radiates a laser beam in a visible region or a near-infrared region at an intensity of several mW (1 to 9 mW, e.g., 3 to 4 mW) and a ND filter whose optical density is in the range of 3 to 4 inclusive is employed as the extinction filter, the intensity of the laser beam entering the eyeball becomes not higher than 10 $\mu$W, which is harmless to the eyeball and is sufficiently high to detect the backscattering light.

DESCRIPTION OF THE PREFERRED EMBODIMENTS

Figure 1:
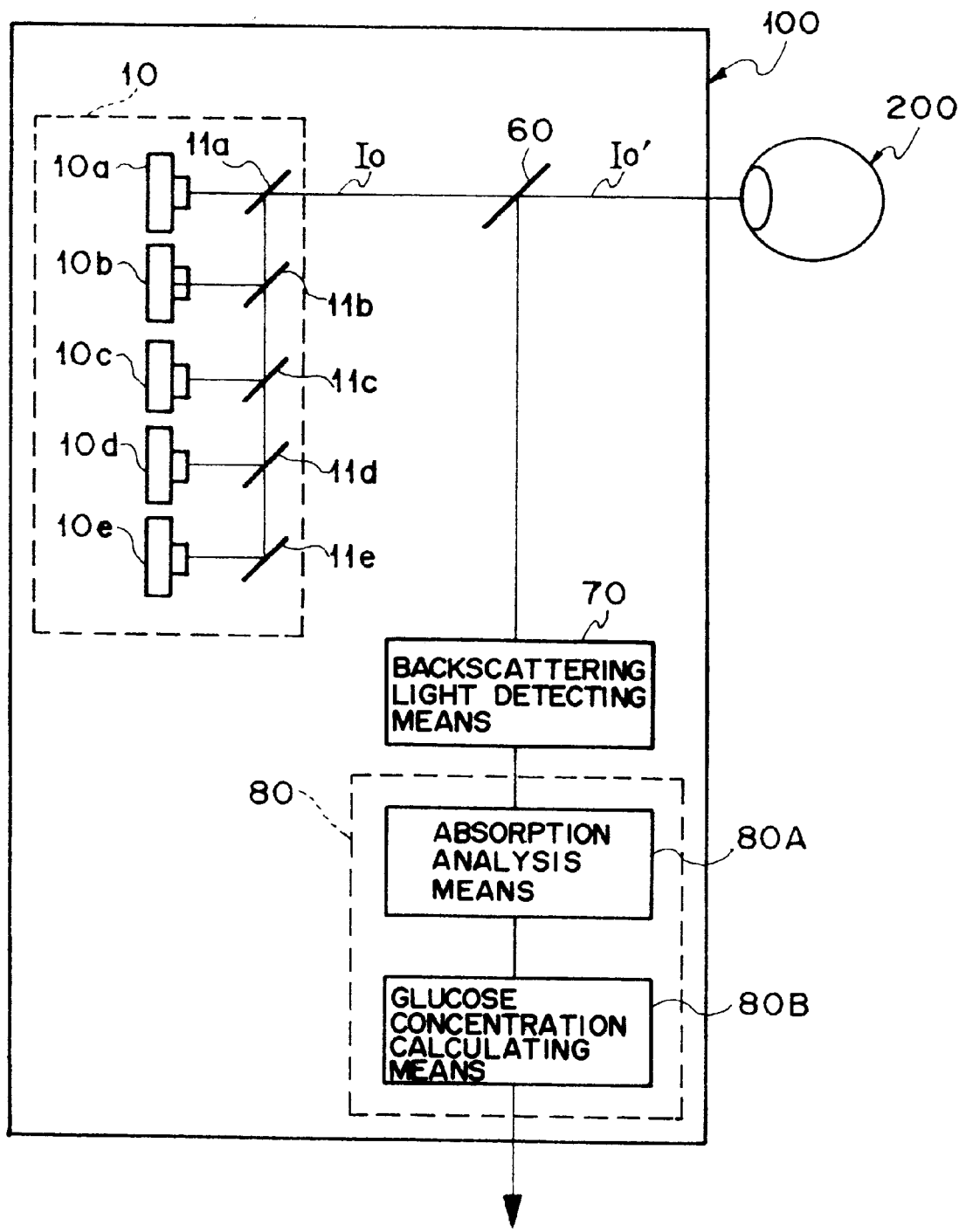
FIG. 1 is a schematic view showing a basic arrangement of a system for carrying out the method in accordance with the first aspect of the present invention, where the glucose concentration in aqueous humor in an anterior chamber is determined on the basis of the absorption properties of the aqueous humor.

In FIG. 1, a glucose concentration measuring system 100 for carrying out the method in accordance with the first aspect of the present invention, where the glucose concentration in aqueous humor in an anterior chamber is determined on the basis of the absorption properties of the aqueous humor, comprises a light source 10. The light source 10 comprises five semiconductor lasers (SLD) 10a, 10b, 10c, 10d and 10e which emit five laser beams at an output intensity of Io in different wavelength bands. The laser beams emitted from the semiconductor lasers 10a to 10e travel along a common optical path by virtue of half-silvered mirrors 11a to 11e disposed in front of the respective semiconductor lasers 10a to 10e. A ND filter 60 having an OD value of 3 is disposed on the common optical path at about 45° to the direction of travel of the laser beam. The laser beam passing through the ND filter 60 impinges upon an eyeball 200. A backscattering light detecting means 70 detects the intensities of backscattering light from predetermined interfaces of the eyeball 200 for each laser beam. An absorption analysis means 80A determines absorption properties of the aqueous humor 220 (FIG. 2) in the anterior chamber on the basis of the intensities of the backscattering light detected by the backscattering light detecting means 70. A glucose concentration calculating means 80B obtains the glucose concentration in the aqueous humor 220 on the basis of the absorption properties of the aqueous humor 220.

Figure 2:
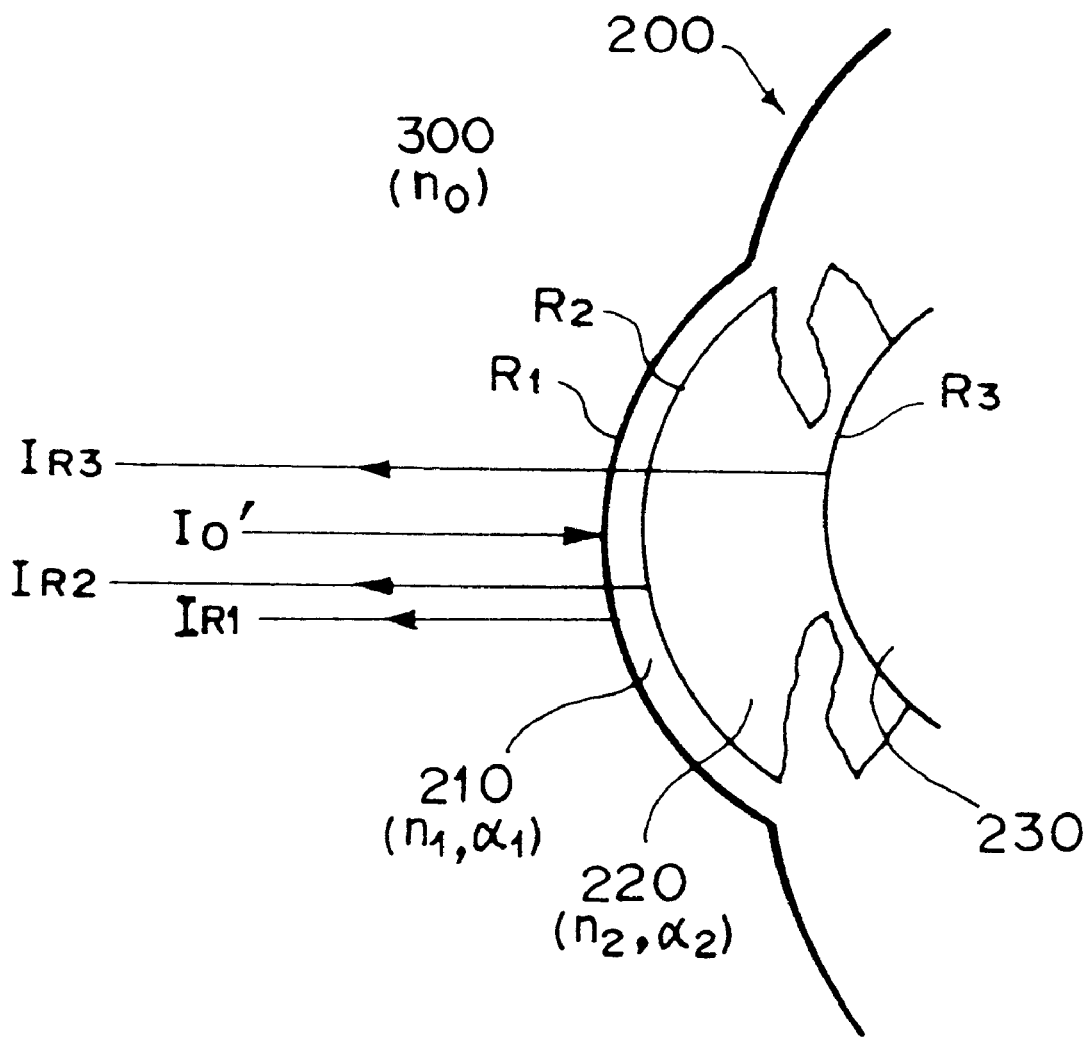
FIG. 2 is a view showing the relation between light entering the eyeball and the backscattering light.

How the absorption analysis means 80A determines the absorption properties of the aqueous humor 220 to a laser beam of a given wavelength will be described with reference to FIG. 2, hereinbelow.

When it is assumed that the intensity of a laser beam of a given wavelength entering the eyeball 200 is Io', the reflectance of the interface between air 300 and the cornea 210 is $R_1$, the reflectance of the interface between the cornea 210 and the aqueous humor 220 (in the anterior chamber) is $R_2$, the reflectance of the interface between the aqueous humor 220 and the lens 230 is $R_3$, the optical absorbance index of the cornea 210 to the incident laser beam for one-way is $\alpha_1$ and the optical absorbance index of the aqueous humor 220 to the incident laser beam for one-way is $\alpha_2$, the intensity $IR_2$ of the backscattering light from the interface between the cornea 210 and the aqueous humor 220 and the intensity $IR_3$ of the backscattering light from the interface between the aqueous humor 220 and the lens 230 are expressed by the following formulae (1) and (2).

$$IR_2 = Io'(1-R_1)^2 R_2 (1-\alpha_1)^2 \quad (1)$$

$$IR_3 = Io'(1-R_1)^2 (1-R_2)^2 R_3 (1-\alpha_1)^2 (1-\alpha_2)^2 \quad (2)$$

Accordingly, the ratio $(IR_3/IR_2)$ of the intensity $IR_3$ of the backscattering light from the interface between the aqueous humor 220 and the lens 230 to the intensity $IR_2$ of the backscattering light from the interface between the cornea 210 and the aqueous humor 220 is expressed as follows.

$$IR_3/IR_2 = (R_3/R_2)(1-R_2)^2 (1-\alpha_2)^2 \quad (3)$$

Since the values of $IR_3$ and $IR_2$ are measured and the values $R_3$ and $R_2$ are known, the value of the optical absorbance index $\alpha_2$ of the aqueous humor 220 to the incident laser beam for one-way (absorption property) can be calculated.

Operation of the glucose concentration measuring system 100 will be described, hereinbelow.

The semiconductor laser 10a first emits a laser beam whose center wavelength is $\lambda 1$ and intensity (Io) is 3 mW. At this time the other semiconductor lasers 10b to 10e are not operated. The laser beam passes through the half-silvered mirror 11a and impinges upon the ND filter 60. The ND filter 60 transmits only a part (Io'=several $\mu$W) of the laser beam and reflects the major part of the laser beam in a direction perpendicular to the direction of travel of the laser beam. Accordingly, the intensity of the laser beam impinging upon the eyeball 200 is several $\mu$W, which is lower than the MPE value which defines ¹⁄₁₀ of the intensity of a laser beam at which incidence of injury is 50% according to JIS C-6802.

The laser beam of an intensity of Io' entering the eyeball 200 is divided into the following four bundles of light (i) to (iv).

(i) light reflected at the interface between air 300 and the cornea 210 (having an intensity of $I_{R1}$)

(ii) light reflected at the interface between the cornea 210 and the aqueous humor 220 (having an intensity of $I_{R2}$)

(iii) light reflected at the interface between the aqueous humor 220 and the lens 230 (having an intensity of $I_{R3}$)

(iv) light passing through the lens 230

Out of these light bundles, light bundles (i) to (iii) emanate from the eyeball in the direction opposite to the incident laser beam as the backscattering light. The backscattering light emanating from the eyeball 220 is almost wholly reflected by the ND filter 60 and enters the backscattering light detecting means 70.

The backscattering light detecting means 70 detects the intensities $I_{R1}$, $I_{R2}$ and $I_{R3}$ of the backscattering light from the interfaces and inputs them into the absorption analysis means 80A.

The absorption analysis means 80A calculates the value of the optical absorbance index $\alpha_2(\lambda 1)$ of the aqueous humor 220 to the laser beam of a wavelength $\lambda 1$ for one-way according to the aforesaid formula (3).

Then the semiconductor laser 10b emits a laser beam whose center wavelength is $\lambda 2$ and intensity (Io) is 3 mW. At this time the other semiconductor lasers 10a and 10c to 10e are not operated. The laser beam is reflected by the half-silvered mirrors 11b and 11a and impinges upon the ND filter 60. The ND filter 60 transmits only a part (Io'=several $\mu$W) of the laser beam and reflects the major part of the laser beam in a direction perpendicular to the direction of travel of the laser beam. Accordingly, the intensity of the laser beam impinging upon the eyeball 200 is several $\mu$W.

Thereafter the intensities $I_{R1}$, $I_{R2}$ and $I_{R3}$ of the backscattering light are detected and the value of the optical absorbance index $\alpha_2(\lambda 2)$ of the aqueous humor 220 to the laser beam of a wavelength $\lambda 2$ for one-way is determined in the manner described above.

In this manner, the semiconductor lasers 10c to 10e are operated in sequence and the values of the optical absorbance indexes $\alpha_2(\lambda 3)$, $\alpha_2(\lambda 4)$ and $\alpha_2(\lambda 5)$ of the aqueous humor 220 to the laser beams of wavelengths $\lambda 3$ to $\lambda 5$ for one-way are determined.

The optical absorbance indexes $\alpha_2(\lambda 1)$ to $\alpha_2(\lambda 5)$ of the aqueous humor 220 are input into the glucose concentration calculating means 80B and the glucose concentration calculating means 80B determines the glucose concentration in the aqueous humor 220 by known near-infrared spectrometry including multivariate analysis on the basis of the optical absorbance indexes $\alpha_2(\lambda 1)$ to $\alpha_2(\lambda 5)$.

As can be understood from the description above, in the glucose concentration measuring system 100, the glucose concentration in the aqueous humor can be determined on the basis of the absorption properties of the aqueous humor and at the same time the ND filter 60 disposed on the optical path of the laser beam between the semiconductor laser and the eyeball reduces the intensity of the laser beam entering the eyeball not higher than a predetermined value of MPE, thereby making harmless the laser beam.

A glucose concentration measuring system 100 in accordance with a more concrete embodiment for carrying out the method in accordance with the first aspect of the present invention will be described with reference to FIG. 3, hereinbelow.

Figure 3:
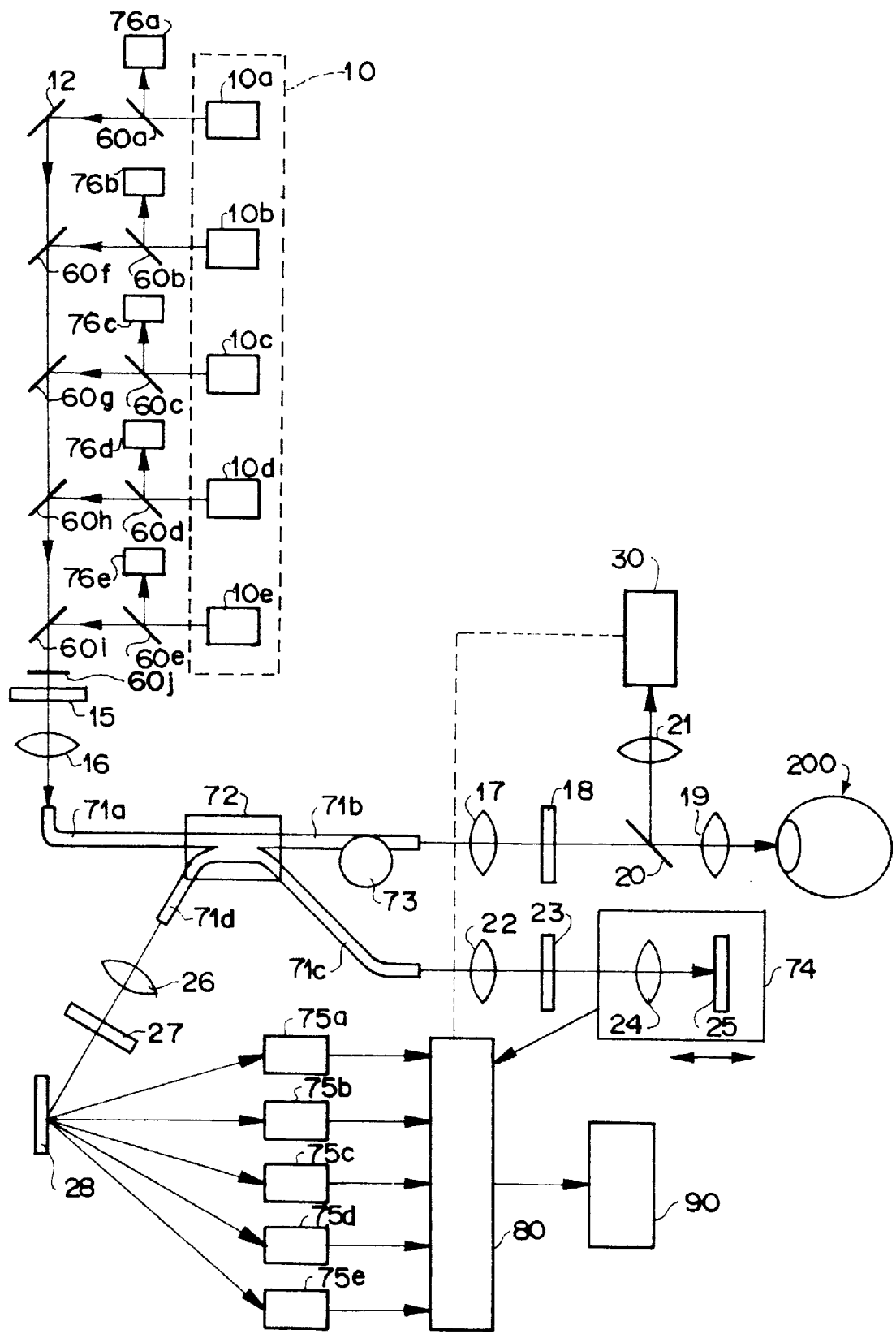
FIG. 3 is a schematic view showing a concrete embodiment of the system shown in FIG. 1.

The glucose concentration measuring system 100 shown in FIG. 3 comprises a light source 10. The light source 10 comprises five semiconductor lasers (SLD) 10a, 10b, 10c, 10d and 10e which emit five laser beams of low coherence which are wide in wavelength band (coherent laser beams which are short in distance of interference). The laser beams respectively emitted from the semiconductor lasers 10a to 10e have center wavelengths of λ1 to λ5, respectively. The laser beams emitted from the respective semiconductor lasers 10a to 10e impinge upon a λ/2 plate 15 after passing through or reflected by a plurality of ND filters 60a to 60j. That is, the laser beam emitted from the semiconductor laser 10a passes through the ND filter 60a (OD=0.5), is reflected by a mirror 12 and impinges upon the λ/2 plate 15 after passing through the ND filters 60f (OD=0.5), 60g (OD=0.5), 60h (OD=0.5), 60i (OD=0.5) and 60j (OD=1.0). The laser beam emitted from the semiconductor laser 10b passes through the ND filter 60b (OD=1.0), is reflected by the ND filter 60f, and impinges upon the λ/2 plate 15 after passing through the ND filters 60g, 60h, 60i and 60j. The laser beam emitted from the semiconductor laser 10c passes through the ND filter 60c (OD=1.5), is reflected by the ND filter 60g, and impinges upon the λ/2 plate 15 after passing through the ND filters 60h, 60i and 60j. The laser beam emitted from the semiconductor laser 10d passes through the ND filter 60d (OD=2.0), is reflected by the ND filter 60h, and impinges upon the λ/2 plate 15 after passing through the ND filters 60i and 60j. The laser beam emitted from the semiconductor laser 10e passes through the ND filter 60e (OD=2.5), is reflected by the ND filter 60i, and impinges upon the λ/2 plate 15 after passing through the ND filter 60j. The λ/2 plate 15 linearly polarizes the laser beams impinging thereupon. The laser beam linearly polarized by the λ/2 plate 15 is caused to enter a first polarization-preserving fibers 71a (to be described later) by a lens 16. Downstream of the lens 16 are disposed first to fourth polarization-preserving fibers 17a to 17d which propagate the laser beam preserving the plane of polarization of the laser beam, a polarization-preserving coupler 72 which combines or divides light propagating through the fibers 17a to 17d with its plane of polarization preserved, a frequency modulator 73 which slightly shifts the frequency of the laser beam which propagates through the second polarization-preserving fiber 71b and impinges upon the eyeball 200 a movable table 74 which changes the length of the optical path of a reference light beam which is divided from the laser beam propagating through the first polarization-preserving fiber 71a by the polarization-preserving coupler 72 and propagates through the third polarization-preserving fiber 71c, photodetectors 75a to 75e which detect light emanating from the fourth polarization-preserving fiber 71d, a radiation thermometer 30 which detects an ambient temperature, a temperature of the outer surface of the cornea 210 and a temperature inside the tympanic membrane (deep temperature), a signal processing circuit 80 which determines the absorption properties of the aqueous humor 220 for the respective wavelengths on the basis of the light intensities detected by the photodetectors 75a to 75e, corrects the absorption properties of the aqueous humor 220 thus obtained according to the temperature distribution detected by the radiation thermometer 30 and calculates the glucose concentration in the aqueous humor 220 on the basis of the corrected absorption properties of the aqueous humor 220, and a display unit 90 which shows the glucose concentration calculated by the signal processing circuit 80.

One of the five semiconductor lasers 10a to 10e emits a laser beam which has a close correlation with the physical length of the anterior chamber as measured along the optical axis thereof (e.g., light of a wavelength of 1790 to 1820 nm or 2230 to 2250 nm). Further the five semiconductor lasers 10a to 10e include a semiconductor laser which emits a laser beam of a wavelength the absorption properties of the aqueous humor 220 to which does not depend upon the temperature of the aqueous humor 220.

The laser beam emanating from the second polarization-preserving fiber 71b (a signal light beam) is collimated by a collimator lens 17, and is converted to circularly polarized light by a λ/4 plate 18. The circularly polarized signal light beam is converged on the eyeball 200 by a condenser lens 19. Infrared rays emitted from the surface of the cornea 210 of the eyeball 200 is reflected by a dichroic 20 and is caused to enter the radiation thermometer 30 by a condenser lens 21. Light emanating from the third polarization-preserving fiber 71c (reference light) is collimated by a collimator lens 22, and is converted to circularly polarized light by a λ/4 plate 23. The circularly polarized reference light is converged on a mirror 25 by a condenser lens 24. The condenser lens 24 and the mirror 25 are mounted on the movable table 74. Light emanating from the fourth polarization-preserving fiber 71d is collimated by a collimator lens 26 and impinges upon a λ/2 plate 27. At this time, the light emanating from the fourth polarization-preserving fiber 71d includes back-scattering light from the eyeball 200 the reference light reflected by the mirror 25 and the laser beam directly enters the fourth polarization-preserving fiber 71d from the first polarization-preserving fiber 71a. The λ2 plate cuts the laser beam directly entering the fourth polarization-preserving fiber 71d from the first polarization-preserving fiber 71a and transmits interference light obtained by interference between the backscattering light from the eyeball 200 and the reference light reflected by the mirror 25. The interference light transmitted through the λ/2 plate 27 is changed with its direction of travel by wavelength band by a diffraction grating 28 to impinge upon one of the photodetectors 75a to 75e. Photodetectors 76a to 76e respectively monitor the intensities of the laser beams as emitted from the semiconductor lasers 10a to 10e.

The frequency modulator 73 shifts the frequency of the light propagating through the second polarization-preserving fiber 71b by, for instance, 1 Hz.

The movable table 74 on which the reflecting mirror 25 and the lens 24 are mounted is movable in the direction of the optical axis of the mirror 25 and the lens 24.

Operation of the glucose concentration measuring system of this embodiment will be described, hereinbelow.

The semiconductor laser 10a first emits a laser beam whose center wavelength is λ1 and intensity is Io. The laser beam impinges upon the ND filter 60a whose OD (optical density) is 0.5. The major part of the laser beam is reflected by the ND filer 60a toward the photodetector 76a and a part of the laser beam passes through the ND filter 60a.

The laser beam passing through the ND filer 60a is reflected by the mirror 12 and passes through the ND filters 60f, 60g, 60h, 60i and 60j. The laser beam is attenuated each time it passes through the ND filters 60a, 60f, 60g, 60h, 60i and 60j and the intensity Io' of the laser beam after passing through the ND filer 60j is lower than the original intensity Io by 3.5 figures.

The laser beam passing through the ND filter 60j is linearly polarized by the λ/2 plate 15 and the linearly polarized laser beam is converged by the lens 16 and is caused to enter the first polarization-preserving fiber 71a.

The laser beam propagates through the first polarization-preserving fiber 71a preserving its plane of polarization and impinges upon the polarization-preserving coupler 72.

The polarization-preserving coupler 72 divides the laser beam into reference light which travels toward the mirror 25 and signal light which travels toward the eyeball 200 while preserving the plane of polarization. That is, the signal light enters the second polarization-preserving fiber 71b and the reference light enters the third polarization-preserving fiber 71c.

The signal light entering the second polarization-preserving fiber 71b is subjected to frequency modulation by the frequency modulator 73 and the frequency of the reference light is shifted by 1 Hz. The frequency-modulated signal light emanates from the second polarization-preserving fiber 71b, is collimated by the collimator lens 17 and is circularly polarized by the $\lambda/4$ plate 18. The circularly polarized signal light passes through the dichroic mirror 20 and is focused by the lens 19 on the interface (R2) between the cornea 210 and the aqueous humor 220 and the interface (R3) between the aqueous humor 220 and the lens 230.

The reference light is reflected by the interface between the cornea 210 and the aqueous humor 220 as a first backscattering light and by the interface between the aqueous humor 220 and the lens 230 as a second backscattering light. The first and second backscattering light passes the lens 19, the dichroic mirror 20, the $\lambda/4$ plate 18 and the lens 17 and enters the second polarization-preserving fiber 71b. Since the direction of circular polarization of the first and second backscattering light is reversed when reflected by the interfaces, the plane of polarization of the first and second backscattering light after passing through the $\lambda/4$ plate 18 is rotated by 90° to the original plane of linear polarization.

The reference light entering the third polarization-preserving fiber 71c is collimated by the lens 22 after emanating from the third polarization-preserving fiber 71c. The collimated reference light is circularly polarized by the $\lambda/4$ plate 23 and is focused on the mirror 25 by the lens 24. The reference light reflected by the mirror 25 travels passing through the lens 24 and the $\lambda/4$ plate 23. Since the direction of circular polarization of the reference light is reversed when reflected by the mirror 25, the plane of polarization of the reflected reference light after passing through the $\lambda/4$ plate 23 is rotated by 90° to the original plane of linear polarization. Then the reflected reference light is caused to enter the third polarization-preserving fiber 71c by the lens 22.

The first and second backscattering light reversing the second polarization-preserving fiber 71b and the reflected reference light reversing the third polarization-preserving fiber 71c is caused to enter the fourth polarization-preserving fiber 71d by the polarization-preserving coupler 72 and is combined. The light propagating through the fourth polarization-preserving fiber 71d is collimated by the lens 26 after emanating from the fourth polarization-preserving fiber 71d. Since the direction of linear polarization of this light has been rotated by 90° to the original linear polarization, this light can pass through the $\lambda/2$ plate 27. The laser beam which directly enters the fourth polarization-preserving fiber 71d from the first polarization-preserving fiber 71a is cut by the $\lambda/2$ plate 27. The light passing through the $\lambda/2$ plate 27 is changed with its direction travel to impinge upon the photodetector 75a. The photodetector 75a converts the intensity of the light impinging thereupon to a DC signal and outputs the DC signal.

When the length of the optical path of the first or second backscattering light to the coupler 72 conforms to that of the optical path of the reflected reference light to the coupler 72, an AC signal at a frequency of 1 Hz (interference signal) is detected by the photodetector 75a.

Since the mirror 25 and the lens 24 on the movable table 74 are movable in the direction of optical axis and accordingly the length of the optical path of the reflected reference light to the coupler 72 is variable, the backscattering light to be interfered with the reference light can be freely selected by changing the length of the optical path of the reflected reference light to the coupler 72 by moving the movable table 74.

That is, when the position of the movable table 74 is adjusted so that the length of the optical path of the reference light conforms to that of the first backscattering light, the reference light interferes with the first backscattering light and interference light obtained by the interference is detected as an AC signal, and when the position of the movable table 74 is adjusted so that the length of the optical path of the reference light conforms to that of the second backscattering light, the reference light interferes with the second backscattering light and interference light obtained by the interference is detected as an AC signal.

Further the optical length of the optical path of light of a wavelength of $\lambda 1$ in the aqueous humor in the anterior chamber can be obtained on the basis of the position of the movable table 74. That is, since the refractive index of the aqueous humor varies with wavelength of light, the optical length of the optical path over which light of a given wavelength travels varies with wavelength of the light.

In this manner, the semiconductor lasers 10b to 10e are operated in sequence and AC signals for the respective wavelengths $\lambda 2$ to $\lambda 5$ are detected by the photodetectors 75b to 75e. Then the signal processing circuit 80 carries out heterodyne operation on the AC signals for the respective wavelengths $\lambda 1$ to $\lambda 5$, whereby the values of the optical absorbance indexes $\alpha_2(\lambda 1)$, $\alpha_2(\lambda 2)$, $\alpha_2(\lambda 3)$, $\alpha_2(\lambda 4)$ and $\alpha_2(\lambda 5)$ of the aqueous humor 220 to the laser beams of wavelengths $\lambda 1$ to $\lambda 5$ are determined.

The radiation thermometer 30 measures the temperature of the outer surface of the cornea 210 or the surface of skin near the eyeball 200 and the temperature of the tympanic membrane. The signal processing circuit 80 calculates the temperature distribution in the eyeball 200 by finite element method or the like on the basis of the measured temperatures.

Then the physical length of the anterior chamber is determined on the basis of the optical absorbance index of the aqueous humor 220 to a wavelength having a close correlation with the physical length of the anterior chamber. At this time, the optical absorbance index of the aqueous humor 220 to the wavelength employed in the operation is hardly affected by the components of the aqueous humor 200.

The signal processing circuit 80 calculates the refractive indexes of the aqueous humor 220 to the wavelengths $\lambda 1$ to $\lambda 5$ on the basis of the physical length and the optical length of the optical paths.

(refractive index=optical length/physical length)

The calculated refractive indexes correspond to the average of the temperature distribution in the aqueous humor 220.

Since the refractive index varies substantially linearly with a temperature range of a few degrees, the signal processing circuit 80 corrects the calculated refractive indexes according to the temperature of the corresponding interfaces obtained from the temperature distribution in the eyeball 200. The correction coefficients to be employed in this correction have been set in advance.

Then the signal processing circuit 80 calculates the reflectances $R_1$, $R_2$ and $R_3$ of the interfaces between air 300 and the cornea 210, between the cornea 210 and the aqueous humor 220 in the anterior chamber and between the aqueous humor 220 and the lens 230 employing the temperature-corrected refractive indexes to the respective wavelengths and subtracts values corresponding to the reflectances from the measured optical absorbance indexes $\alpha_2(\lambda 1)$, $\alpha_2(\lambda 2)$, $\alpha_2(\lambda 3)$, $\alpha_2(\lambda 4)$ and $\alpha_2(\lambda 5)$. Since the resultant optical absorbance indexes $\alpha_2(\lambda 1)'$, $\alpha_2(\lambda 2)'$, $\alpha_2(\lambda 3)'$, $\alpha(\lambda 4)'$ and $\alpha_2(\lambda 5)'$ include variations with temperature, the signal processing circuit 80 carries out temperature correction.

Figure 4:
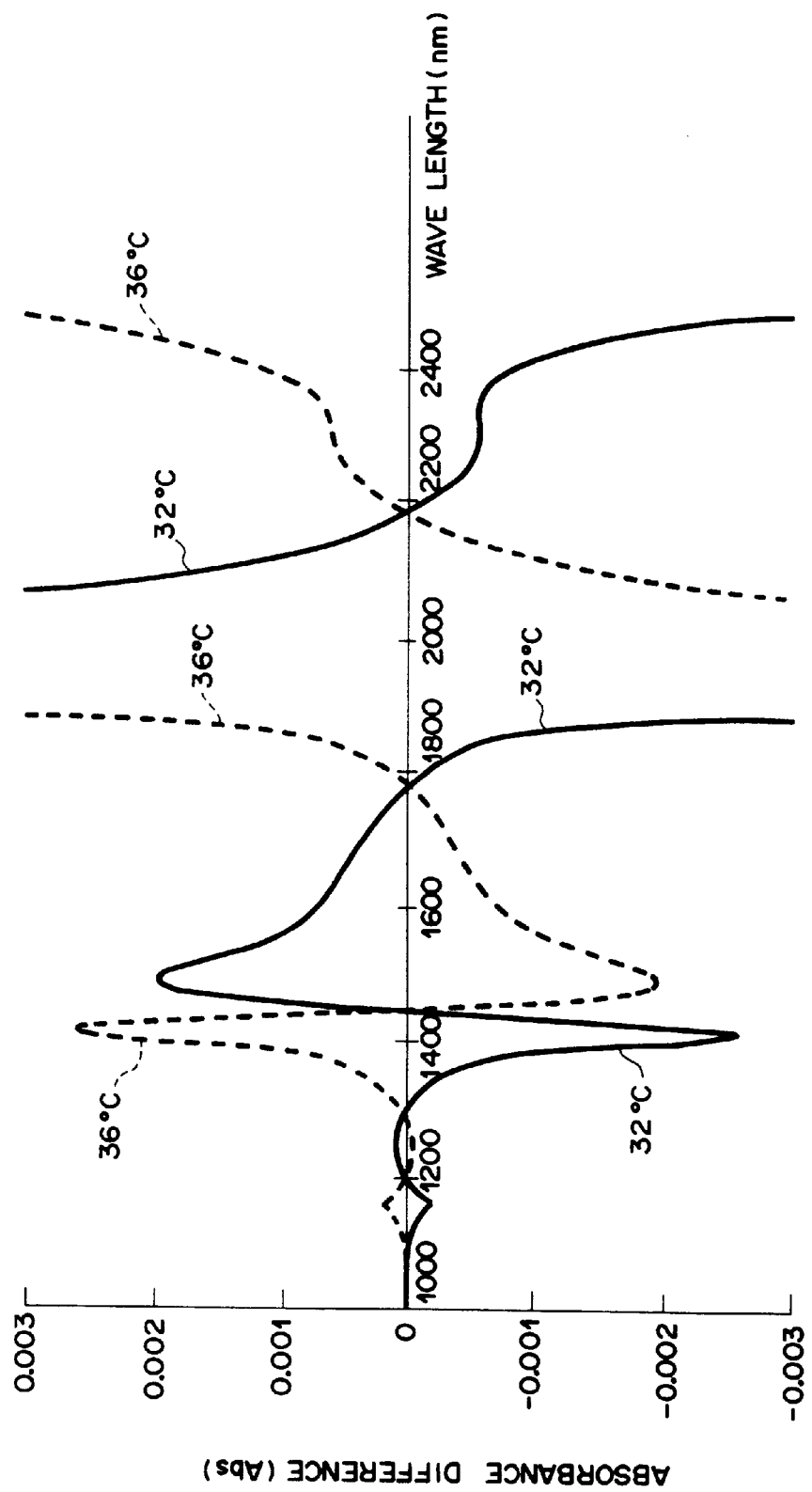
FIG. 4 is a view showing temperature-dependency of light beams of various wavelengths.

The temperature-dependency of the optical absorbance index is linear in an expected temperature range. The resultant optical absorbance indexes $\alpha_2(\lambda 1)'$, $\alpha_2(\lambda 2)'$, $\alpha_2(\lambda 3)'$, $\alpha_2(\lambda 4)'$ and $\alpha_2(\lambda 5)'$ are corrected according to the temperatures of the interfaces between the cornea 210 and the aqueous humor 220 and between the aqueous humor 220 and the lens 230. The temperature coefficients is determined referring to a lookup table or a function which has been stored in the signal processing circuit 80 and in which the temperature coefficient is related to the temperature and the optical absorbance index for each wavelength. For example, FIG. 4 shows differences of the optical absorbance indexes at 32° and 36° from those at 34°.

The signal processing circuit 80 determines the glucose concentration in the aqueous humor 220 by known near-infrared spectrometry including multivariate analysis on the basis of the temperature-corrected optical absorbance indexes to the respective wavelengths.

As can be understood from the description above, in the glucose concentration measuring system 100 of this embodiment, the glucose concentration in the aqueous humor can be determined on the basis of the absorption properties of the aqueous humor and at the same time the ND filters disposed on the optical path of the laser beam between the semiconductor laser and the eyeball reduce the intensity of the laser beam entering the eyeball not higher than a predetermined value of MPE, thereby making harmless the laser beam. Further, in this particular embodiment, the glucose concentration can be accurately measured irrespective of variation in the ambient temperature and/or the temperature of the patient.

It is possible that the correlation between the glucose concentration in the aqueous humor in the anterior chamber as measured by this system and the blood glucose concentration obtained by the conventional invasive method or theoretically obtained for each patient is stored in advance in the signal processing circuit 80 as, for instance, a conversion table and the blood glucose concentration is determined on the basis of the glucose concentration in the aqueous humor in the anterior chamber as measured by this system according to the stored correlation therebetween.

Though, in the glucose concentration measuring system in accordance with this embodiment, low coherent light is employed and the length of the optical path of the reference light is adjusted substantially equal to that of the signal light with the frequency of the signal light impinging upon the eyeball 200 uniformly shifted so that the backscattering light from a desired interface of the eyeball 200 interferes with the reference light, thereby detecting the backscattering light from a plurality of interfaces separately from each other, the glucose concentration measuring system in accordance with the third aspect of the present invention for carrying out the method in accordance with the first aspect of the present invention need not be limited to such an arrangement.

For example, the glucose concentration measuring system in accordance with the third aspect of the present invention may employ a system for separately detecting the backscattering light from a predetermined interfaces of the eyeball which system comprises a semiconductor laser which emits a plurality of coherent laser beams which are different from each other in wavelength band and are frequency-swept with time in a saw tooth shape, a beam splitter means which divides each of the laser beams emitted from the semiconductor laser into a signal light beam and a reference light beam travelling along two different optical paths so that the signal light beam impinges upon the eyeball, a wavefront matching means which brings first backscattering light of the signal light beam generated by the interface between the cornea and the aqueous humor into wavefront matching with the coherent reference light beam which is different from the first backscattering light in frequency and is emitted from the semiconductor laser with a time difference based on the difference between the length of the optical path of the signal light beam and the first backscattering light and the length of the optical path of the reference light beam and brings second backscattering light of the signal light beam generated by the interface between the aqueous humor and the lens into wavefront matching with the coherent reference light beam which is different from the second backscattering light in frequency and is emitted from the semiconductor laser with a time difference based on the difference between the length of the optical path of the signal light beam and the second backscattering light and the length of the optical path of the reference light beam, a photodetector which photoelectrically detects the intensity of first interference light obtained by the wavefront matching between the first backscattering light and the reference light beam having a slight frequency difference relative to the first backscattering light and the intensity of second interference light obtained by the wavefront matching between the second backscattering light and the reference light beam having a slight frequency difference relative to the first backscattering light, and a heterodyne operation means which determines the intensities of the first and second backscattering light on the basis of the intensities of the first and second interference light.

Further the system for separately detecting the backscattering light from a predetermined interfaces of the eyeball may comprise a semiconductor laser which emits a plurality of laser beams which are in the form of ultrashort pulse light and are different from each other in wavelength, and a backscattering light measuring means such as a streak camera which causes the laser beams to enter the eyeball and separately measures in time series intensities of first backscattering light of the laser beam generated by the interface between the cornea and the aqueous humor and second backscattering light of the laser beam generated by the interface between the aqueous humor and the lens.

A glucose concentration measuring system 100 in accordance with another embodiment for carrying out the method in accordance with the first aspect of the present invention will be described with reference to FIG. 5, hereinbelow. In this embodiment, the glucose concentration in the aqueous humor in an anterior chamber is determined on the basis of the refractive index of the aqueous humor.

Figure 5:
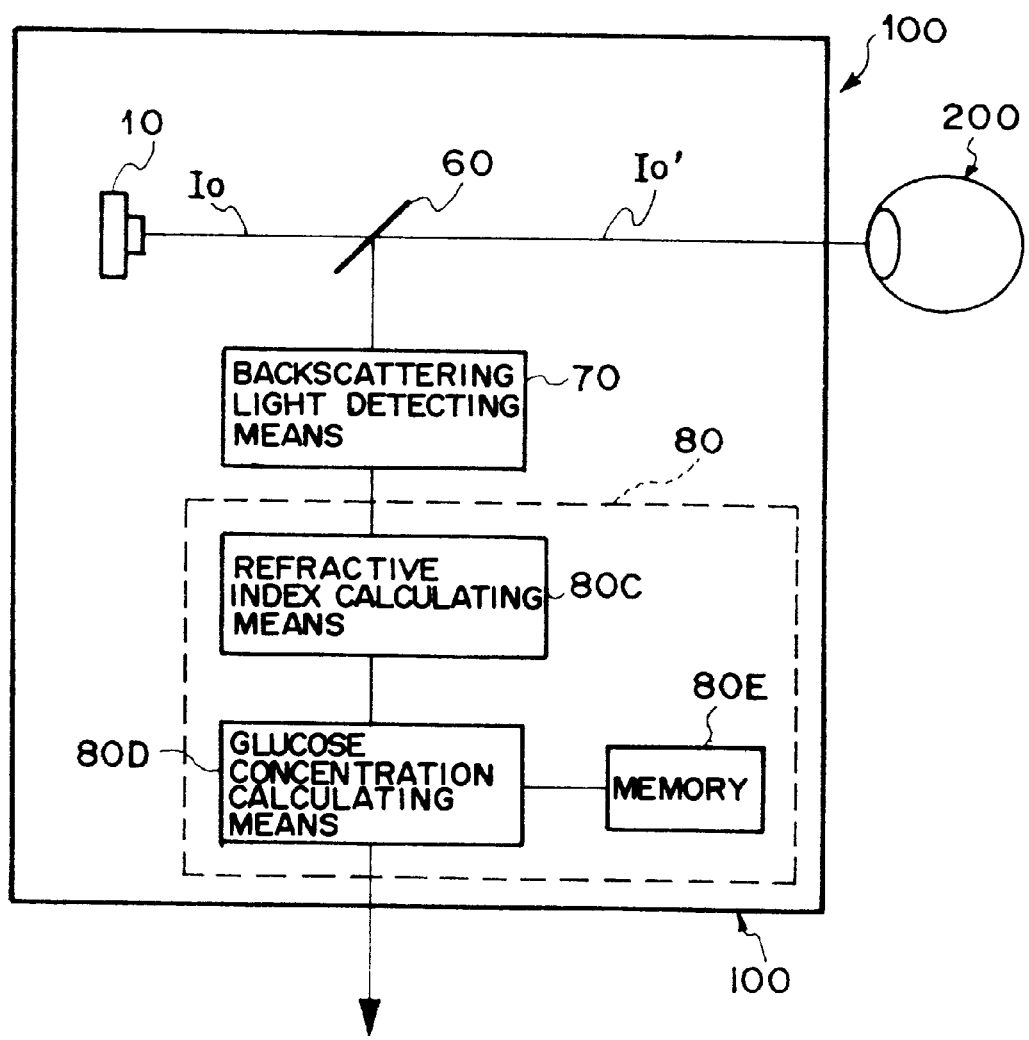
FIG. 5 is a schematic view showing a basic arrangement of a system for carrying out the method in accordance with the first aspect of the present invention, where the glucose concentration in aqueous humor in an anterior chamber is determined on the basis of the refractive index of the aqueous humor.
Figure 6:
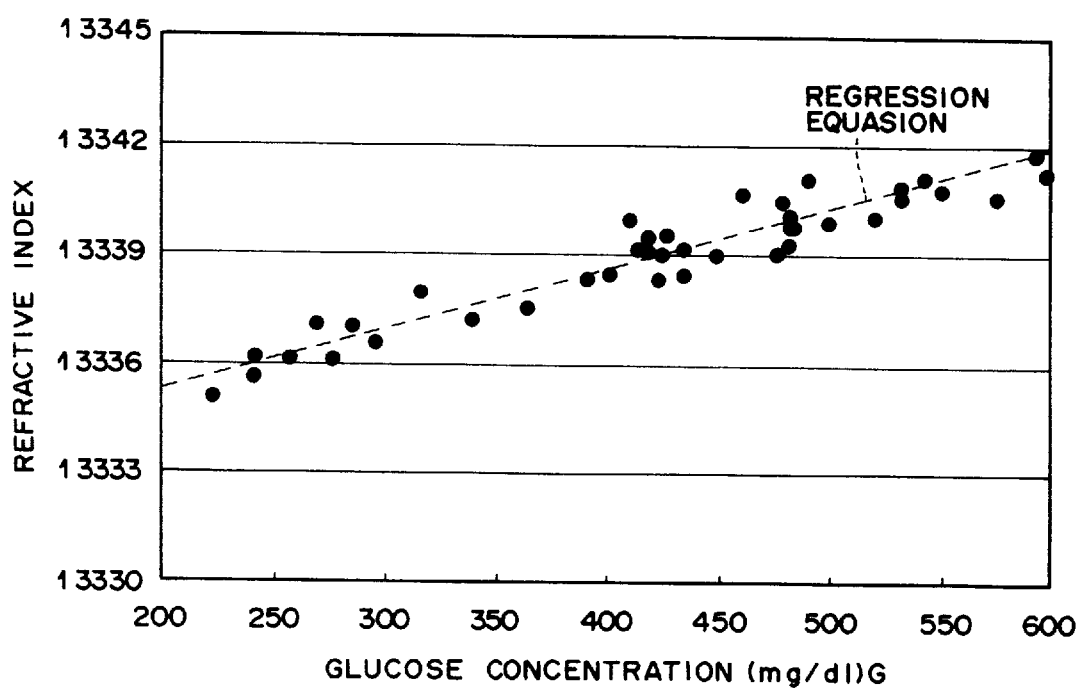
FIG. 6 is a view showing a correlation between the refractive index of the aqueous humor in an anterior chamber and the glucose concentration therein.

In FIG. 5, the glucose concentration measuring system 100 of this embodiment comprises a semiconductor laser 10 which emits a laser beam at an intensity of Io, a ND filter 60 having an OD value of 3 which is disposed on the optical path of the laser beam at about 45° to the direction of travel of the laser beam, a backscattering light detecting means 70 which detects the intensities of backscattering light from predetermined interfaces of the eyeball 200, a refractive index calculating means 80C which calculates the refractive index of the aqueous humor 220 in the anterior chamber on the basis of the intensities of the backscattering light detected by the backscattering light detecting means 70, a memory 80E which stores the correlation between the refractive index of the aqueous humor 220 and the glucose concentration therein shown in FIG. 6, and a glucose concentration calculating means 80D which calculates the glucose concentration in the aqueous humor 220 on the basis of the calculated refractive index of the aqueous humor 220 according to the correlation between the refractive index of the aqueous humor and the glucose concentration therein stored in the memory 80E.

The correlation shown in FIG. 6 has been empirically determined and can be expressed by the following regression equation (correlation coefficient: 0.9516).

$$n_2 = 1.33322 + 1.6 \times 10^{-6} \times G$$

wherein G represents the glucose concentration (mg/dl).

How the refractive index calculating means 80C determines the refractive index of the aqueous humor 220 to a laser beam of a given wavelength will be described with reference to FIG. 2, hereinbelow.

When it is assumed that the refractive index of air is $n_0$, and the refractive index of the cornea 210 is $n_1$, the intensity $IR_1$ of the reflected light (first backscattering light) from the interface between the cornea 210 and air 300 is expressed by the following formula (4).

$$IR_1 = Io'\{(n_0 - n_1)/(n_0 + n_1)\}^2 \tag{4}$$

When the reflectance $R_1$ of the interface between air 300 and the cornea 210 is represented by $\{(n_0 - n_1)/(n_0 + n_1)\}^2$, the reflectance of the interface between the cornea 210, the intensity of the reflected light (second backscattering light) from the interface between the cornea 210 and the aqueous humor 220 is represented by $IR_2$, the absorbance of the cornea 210 is represented by a, the thickness of the cornea 210 is represented by b and the refractive index of the aqueous humor 220 is represented by $n_2$, $$I_{R2} = Io'(1-R_1)^2 10^{-2ad}\{(n_1 - n_2)/(n_1 + n_2)\}^2 \tag{5}$$

Accordingly, $$n_2 = (-2k_{n1} - 2_{n1} + 4k^{1/2}n_1)/\{2(k-1)\} \tag{6}$$

or $$n_2 = (-2k_{n1} - 2_{n1} - 4k^{1/2}n_1)/\{2(k-1)\} \tag{7}$$

wherein $k = (I_{R2}/Io')$.

Thus there are two solutions for the refractive index $n_2$, those represented by formulae (6) and (7). Since the solution given by formula (6) conforms to the data obtained by experiments, the refractive index $n_2$ is determined according to formula (6).

Operation of the glucose concentration measuring system 100 will be described, hereinbelow.

The semiconductor laser 10 emits a laser beam whose intensity (Io) is 3 mW. The laser beam impinges upon the ND filter 60. The ND filter 60 transmits only a part (Io'= several μW) of the laser beam and reflects the major part of the laser beam in a direction perpendicular to the direction of travel of the laser beam. Accordingly, the intensity of the laser beam impinging upon the eyeball 200 is several μW, which is lower than the MPE value.

The laser beam of an intensity of Io' entering the eyeball 200 is divided into the following four bundles of light (i) to (iv).

(i) light reflected at the interface between air 300 and the cornea 210 (having an intensity of $I_{R1}$)

(ii) light reflected at the interface between the cornea 210 and the aqueous humor 220 (having an intensity of $I_{R2}$)

(iii) light reflected at the interface between the aqueous humor 220 and the lens 230 (having an intensity of $I_{R3}$)

(iv) light passing through the lens 230

Out of these light bundles, light bundles (i) to (iii) emanate from the eyeball 200 in the direction opposite to the incident laser beam as the backscattering light. The backscattering light emanating from the eyeball 220 is almost wholly reflected by the ND filter 60 and enters the backscattering light detecting means 70.

The backscattering light detecting means 70 detects the intensities $I_{R1}$, $I_{R2}$ and $I_{R3}$ of the backscattering light from the interfaces and inputs them into the refractive index calculating means 80C. The refractive index calculating means 80C calculates the refractive index $n_2$ of the aqueous humor 220 to the incident laser beam according to the aforesaid formula (6).

The refractive index $n_2$ of the aqueous humor 220 thus determined is input into the glucose concentration calculating means 80D and the glucose concentration calculating means 80D determines the glucose concentration in the aqueous humor 220 on the basis of the input refractive index $n_2$ of the aqueous humor 220 according to the correlation stored in the memory 80E.

As can be understood from the description above, in the glucose concentration measuring system 100, the glucose concentration in the aqueous humor can be determined on the basis of the refractive index of the aqueous humor and at the same time the ND filter 60 disposed on the optical path of the laser beam between the semiconductor laser and the eyeball reduces the intensity of the laser beam entering the eyeball not higher than a predetermined value of MPE, thereby making harmless the laser beam. In the case of the embodiments described above in conjunction with FIGS. 1 and 3 where the glucose concentration is determined on the basis of measured absorption properties of the aqueous humor 220, it is necessary to measure the absorption properties repeatedly by use of a plurality of laser beams (typically not less than 5) of different wavelengths in order to reduce measurement error due to a number of light absorbing components in the aqueous humor. However in the glucose concentration measuring system of this embodiment, since the glucose concentration is related to the refractive index to a laser beam of a single wavelength, the measuring time is greatly shortened.

A glucose concentration measuring system 100 in accordance with a more concrete embodiment for carrying out the method in accordance with the first aspect of the present invention, where the glucose concentration in the aqueous humor is determined on the basis of the refractive index of the aqueous humor will be described with reference to FIG. 7, hereinbelow.

Figure 7:
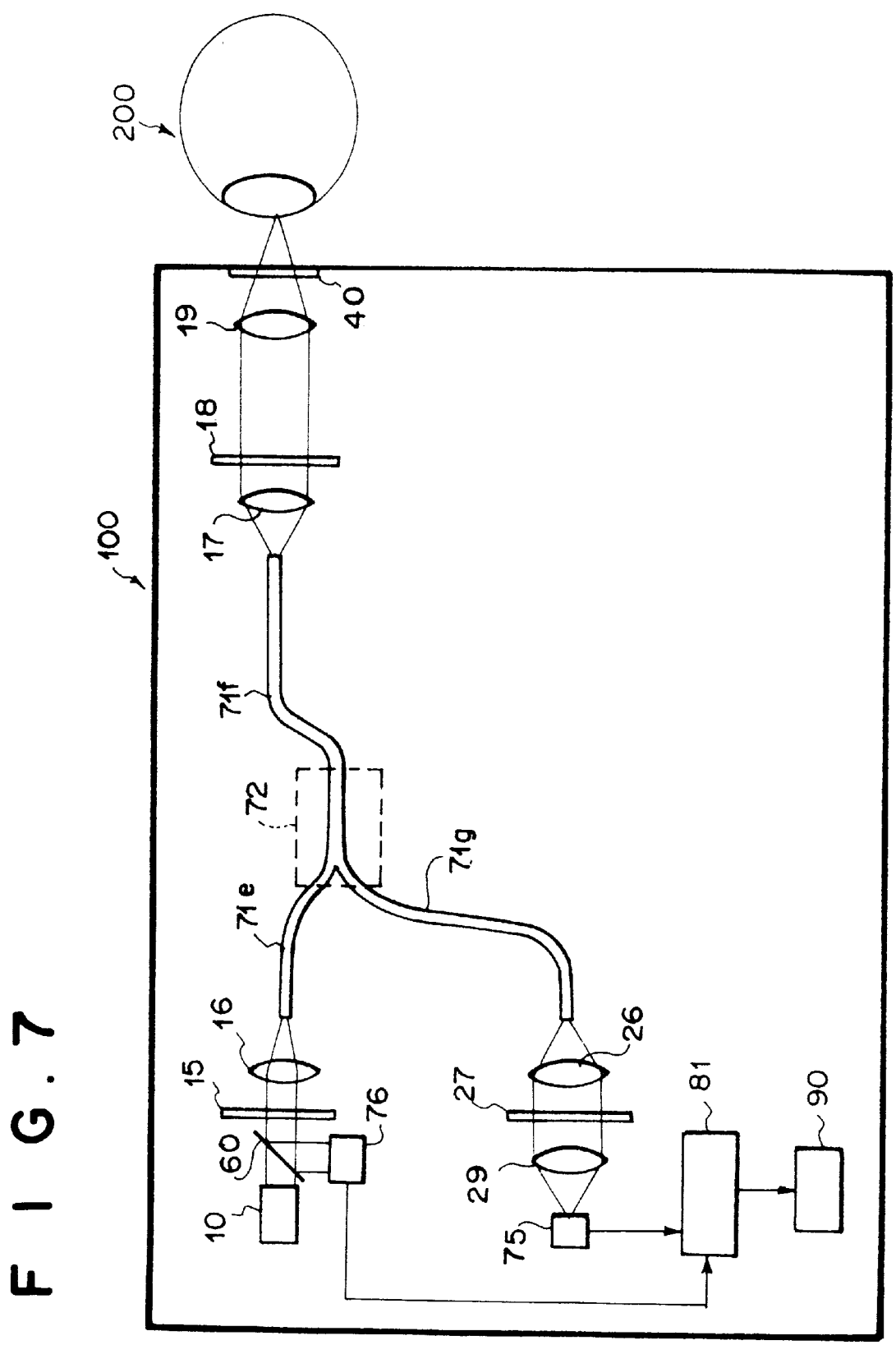
FIG. 7 is a schematic view showing a concrete embodiment of the system shown in FIG. 5.

In FIG. 7, the glucose concentration measuring system in accordance with this embodiment comprises a frequency-sweep semiconductor laser 10 which emits a laser beam which is frequency-swept with time in a saw tooth shape, has a constant wavelength in a visible region and is 3 to 4 mW (Io), an ND filter 60 (OD=3.0) which transmits a part of the laser beam emitted from the semiconductor laser 10, a λ/2 plate 15 which linearly polarizes the laser beams passing through the ND filer 60, a lens 16 which converges the laser beam linearly polarized by the λ/2 plate 15, first to third polarization-preserving fibers 71e, 71f and 71g which propagate the laser beam preserving the plane of polarization of the laser beam, a polarization-preserving coupler 72 which transmits light propagating through one of the fibers 71e to 71g to another with its plane of polarization preserved, a collimator lens 17 which collimates the light emanating from the second polarization-preserving fiber 71f, a λ/4 plate 18 which circularly polarizes the collimated light, a condenser lens 19 which converges the circularly polarized light on the interfaces between air 300 and the cornea 210 and between the cornea 210 and the aqueous humor 220, an exterior light cut filter 40 which transmits only reflected light from the eyeball 200 (including the reflected light (first backscattering light) from the interfaces between air 300 and the cornea 210 and the reflected light (second backscattering light) from the interface between the cornea 210 and the aqueous humor 220), a collimator lens 26 which collimates light which returns from the second polarization-preserving fiber 71f and emanates from the third polarization-preserving fiber 71g (including the signal light (first and second backscattering light) and the reference light reflected by the λ/4 plate 18), a λ2 plate 27 which cuts the laser beam directly entering the third polarization-preserving fiber 71g from the first polarization-preserving fiber 71e and transmits interference light obtained by interference between the backscattering light from the eyeball 200 and the reference light reflected by the λ/4 plate 18, a condenser lens 29 converges the interference light transmitted through the λ/2 plate 27 on a photodetector 75, a signal processing circuit 81 which calculates the refractive index of the aqueous humor 220 on the basis of the light intensities detected by the photodetector 75, and determines the glucose concentration G in the aqueous humor 220 on the basis of the calculated refractive index $n_2$ of the aqueous humor 220 according to the correlation stored therein, a display unit 90 which shows the glucose concentration calculated by the signal processing circuit 81, and a photodetector 76 which monitors the intensity of the laser beam reflected by the ND filter 60.

The signal processing circuit 81 functions as the refractive index calculating means 80C, the glucose concentration calculating means 80D and the memory 80E shown in FIG. 5.

Operation of the glucose concentration measuring system of this embodiment will be described hereinbelow.

Figure 8:
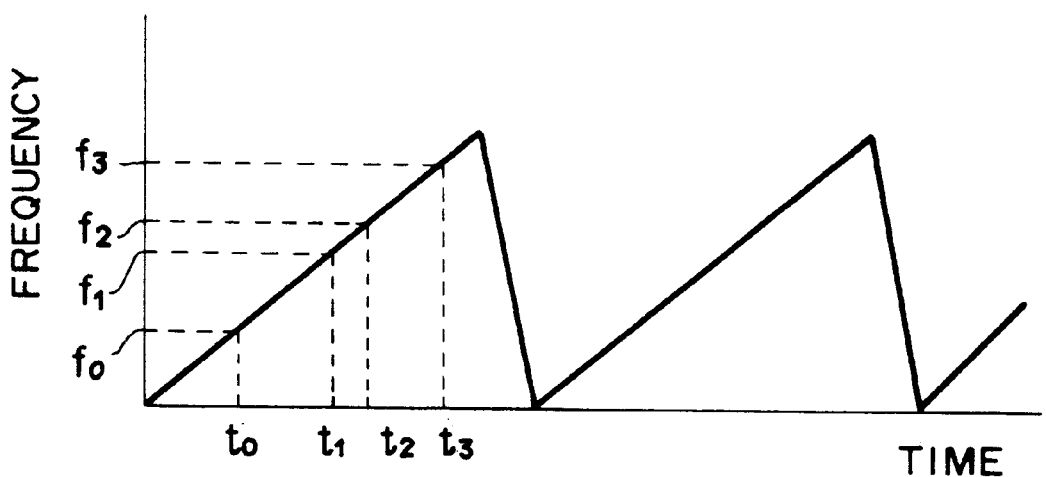
FIG. 8 is a graph showing frequency sweep.

The semiconductor laser 10 emits a laser beam whose intensity is Io. The laser beam is swept with its frequency along a time axis as shown in FIG. 8, and it is assumed that the frequency of the laser beam at the time $t_0$ at which the laser beam is emitted from the laser 10 is $f_0$.

The laser beam whose intensity Io and frequency is $f_0$ impinges upon the ND filter 60 whose OD (optical density) is 3.0. The major part of the laser beam is reflected by the ND filer 60 toward the photodetector 76 and a part of the laser beam (intensity of Io') passes through the ND filter 60.

The laser beam passing through the ND filer 60 is linearly polarized by the λ/2 plate 15 and the linearly polarized laser beam is caused to enter the first polarization-preserving fiber 71e. The laser beam propagates through the first polarization-preserving fiber 71e and is caused to enter the second polarization-preserving fiber 71f by the polarization-preserving coupler 72 with its plane of polarization preserved as it is linear. The light entering the second polarization-preserving fiber 71f emanates from the second polarization-preserving fiber 71f, is collimated by the collimator lens 17 and is circularly polarized by the λ/4 plate 18. The circularly polarized light is focused by the lens 19 on the interface between air 300 and the cornea 210 and the interface between the cornea 210 and the aqueous humor 220. The intensity of light impinging upon the eyeball 200 is Io'.

The incident light is reflected by the interface between air 300 and the cornea 210 as a first backscattering light and by the interface between the cornea 210 and the aqueous humor 220 as a second backscattering light. The first and second backscattering light passes through the exterior light cut filter 20, the λ/4 plate 18 and the lens 17 and enters the second polarization-preserving fiber 71f.

The plane of polarization of the first and second backscattering light after passing through the λ/4 plate 18 is rotated by 90° to the original plane of linear polarization. The first and second backscattering light enters the polarization-preserving coupler 72.

A part of the light emanating from the second polarization-preserving fiber 71f is reflected by the λ/4 plate 18 and enters the second polarization-preserving fiber 71f to enter the polarization-preserving coupler 72 as reference light.

The difference in the length of the optical path between the first and second backscattering light reflected by the interfaces of the eyeball 200 and the reference light reflected by the λ/4 plate 18 will be discussed, hereinbelow. The optical path of the first backscattering light is longer than that of the reference light by a distance twice the distance between the λ/4 plate 18 and the interface between air 300 and the cornea 210 and the optical path of the second backscattering light is longer than that of the reference light by a distance twice the distance between the λ/4 plate 18 and the interface between the cornea 210 and the aqueous humor 220.

That is, the first backscattering light meets the reference light at the λ/4 plate 18 earlier than the second backscattering light. This time difference depends upon the distance twice the thickness of the cornea 210.

On the other hand, frequency-swept laser beam is continuously emitted from the semiconductor laser 10 and continuously reaches the λ/4 plate 18.

As a result, the first backscattering light (frequency of $f_0$) generated by the laser beam emitted from the semiconductor laser 10 at time to meets the reference light at a frequency of $f_1$ emitted from the semiconductor laser 10 at time $t_1$ (FIG. 8) and is brought into wavefront matching with the reference light. Accordingly the interference light generated by the wavefront matching beats at a frequency corresponding to the frequency difference therebetween ($f_1-f_0$).

The second backscattering light (frequency of $f_0$) generated by the laser beam emitted from the semiconductor laser 10 at time $t_0$ meets the reference light at a frequency of $f_2$ emitted from the semiconductor laser 10 at time $t_2$ later than time $t_1$ by time 2d/c which is required for the light to travel the distance 2d twice the thickness of the cornea 210 (c representing velocity of light) and is brought into wavefront matching with the reference light. Accordingly the interference light generated by the wavefront matching beats at a frequency corresponding to the frequency difference therebetween ($f_2-f_0$).

Though a laser beam whose frequency varies time to time is continuously emitted from the semiconductor laser 10, the frequencies of the interference is kept constant since the difference in the length of the optical path between the first and second backscattering light and the reference light is unchanged.

The interference light which is generated by interference between the first backscattering light and the reference light and beats at the difference frequency ($f_1-f_0$) and the interference light which is generated by interference between the second backscattering light and the reference light and beats at the difference frequency ($f_2-f_0$) are led to the photodetector 75 through the polarization-preserving coupler 72 and the third polarization-preserving fiber 71g.

The photodetector 75 calculates the intensities of the first and second backscattering light on the basis of the intensities of the interference light by heterodyne processing and calculates the difference in the length of the optical path between the first and second backscattering light, i.e., the thickness of the cornea 210, on the basis of the difference in frequency between the interference light and the inclination in the frequency sweep.

The signal processing circuit 81 calculates the refractive index $n_2$ of the aqueous humor 220 according to the aforesaid formula on the basis the intensities $I_{R1}$ and $I_{R2}$ of the first and second backscattering light and the thickness d of the cornea 210 thus obtained and the known values of the refractive indexes $n_0$ and $n_1$, reflectances $R_1$ and $R_2$ and the absorbance a, and obtains the glucose concentration G in the aqueous humor 220 in the anterior chamber according to the correlation between the refractive index $n_2$ of the aqueous humor 220 and the glucose concentration G therein. Then the display unit 90 shows the calculated glucose concentration G.

As can be understood from the description above, in the glucose concentration measuring system 100 of this embodiment, the glucose concentration in the aqueous humor can be determined on the basis of the absorption properties of the aqueous humor and at the same time the ND filters disposed on the optical path of the laser beam between the semiconductor laser and the eyeball reduce the intensity of the laser beam entering the eyeball not higher than a predetermined value of MPE, thereby making harmless the laser beam.

Though, in the glucose concentration measuring system in accordance with this embodiment, frequency-swept coherent light is employed in order to detect the backscattering light from a plurality of interfaces separately from each other, the glucose concentration measuring system in accordance with the third aspect of the present invention for carrying out the method in accordance with the first aspect of the present invention need not be limited to such an arrangement.

For example, the glucose concentration measuring system in accordance with the third aspect of the present invention may employ one of the following systems for separately detecting the backscattering light from a predetermined interfaces of the eyeball.

(a) A system comprising a semiconductor laser which emits a laser beam of low coherence, a beam splitter means which divides the laser beam emitted from the semiconductor laser into a signal light beam and a reference light beam travelling along two different optical paths so that the signal light beam impinges upon the eyeball, a light modulator means which modulates at least one of the signal light beam and the reference light beam in such a way that a slight frequency difference is produced between them, an optical length controlling means for controlling the length of the optical path of the reference light beam, a wavefront matching means which brings each of first backscattering light of the signal light beam generated by the interface between the cornea and air and second backscattering light of the signal light beam generated by the interface between the aqueous humor and the cornea into wavefront matching with the reference light beam, a photodetector which photoelectrically detects the intensity of first interference light obtained by the wavefront matching between the first backscattering light and the reference light beam and the intensity of second interference light obtained by the wavefront matching between the second backscattering light and the reference light beam, and a heterodyne operation means which determines the intensities of the first and second backscattering light on the basis of the intensities of the first and second interference light.

(b) A system comprising a semiconductor laser which emits a laser beam in the form of ultrashort pulse light, and a backscattering light measuring means which causes the laser beam to enter the eyeball and separately measures in time series intensities of first backscattering light of the laser beam generated by the interface between the cornea and air and second backscattering light of the laser beam generated by the interface between the aqueous humor and the cornea.

(c) A system comprising a semiconductor laser which projects a laser beam onto an eyeball which has been in a predetermined position, a confocal optical system which spatially separates first backscattering light of the laser beam generated by the interface between the cornea and air and second backscattering light of the laser beam generated by the interface between the aqueous humor and the cornea from each other, the confocal optical system being capable of having one focal point on each of the interfaces with a pin hole disposed on the other focal point, and a photodetector which photoelectrically detects the intensity of the first and second backscattering light spatially separated from each other by the confocal optical system.

A glucose concentration measuring system 100 which carries out the method in accordance with the second aspect of the present invention will be described with reference to FIG. 9, hereinbelow.

Figure 9:
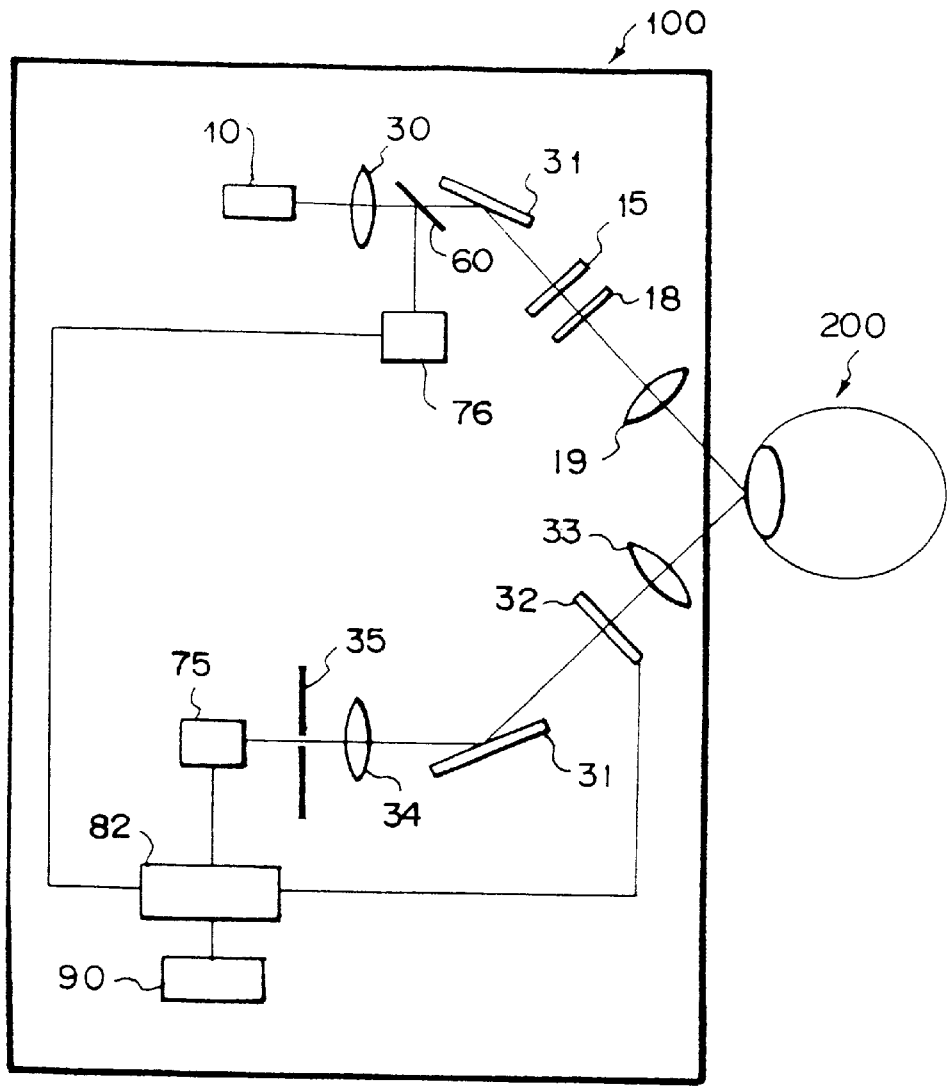
FIG. 9 is a schematic view showing a system for carrying out the method in accordance with the second aspect of the present invention.
Figure 10:
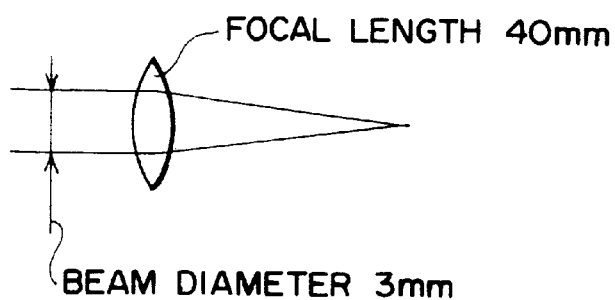
FIG. 10 is a schematic view showing an optical system which can be employed in the present invention.

In FIG. 9, the glucose concentration measuring system 100 comprises a semiconductor laser 10 which emits a laser beam in a visible region (<1400 nm) having a constant frequency at an intensity of 3 to 4 mW (Io), a collimator lens 30 which collimates the laser beam emitted from the semiconductor laser 10, an ND filter 60 (having an optical density of 3.0) which transmits a part of the collimated laser beam, a mirror 31 which reflects the laser beam passing through the ND filter 60 at a predetermined angle, a $\lambda/2$ plate 15 which linearly polarizes the reflected laser beam, a $\lambda/4$ plate 18 which circularly polarizes the linearly polarized laser beam, a lens 19 which causes the circularly polarized laser to impinge upon the interface between the cornea 210 and the aqueous humor 220 at a preset angle of incidence in the form of an elliptically polarized light, a combination of an analyzer 32 and a photodetector 75 which detect the azimuth and the amplitude of elliptically polarized backscattering light reflected from the interface between the cornea 210 and the aqueous humor 220, a mirror 31 which reflects at a predetermined angle the backscattering light passing through the analyzer 32, a confocal optical system formed of condenser lenses 33 and 34 and a pin hole 35 which spatially separate the backscattering light reflected from the interface between the cornea 210 and the aqueous humor 220, a signal processing circuit 82 which calculates the refractive index $n_2$ of the aqueous humor 220 on the basis of the state of elliptical polarization (the azimuth and the amplitude) of the backscattering light and said angle of incidence of the circularly polarized laser beam and determines the glucose concentration G in the aqueous humor 220 on the basis of the calculated refractive index $n_2$ of the aqueous humor 220 according to the correlation stored therein, a display unit 90 which shows the glucose concentration calculated by the signal processing circuit 82, and a photodetector 76 which monitors the intensity of the laser beam reflected by the ND filter 60.

For example, the refractive index $n_2$ of the aqueous humor in the anterior chamber can be determined on the basis of the state of elliptical polarization of the backscattering light by use of the principle of ellipsometer. That is, an amplitude ratio ψ and a phase difference Δ are obtained from the ellipticity ρ and the azimuth φ of elliptical polarization of the backscattering light detected by the analyzer 32 and the photodetector 75 and the refractive index $n_2$ of the aqueous humor is given by the following formula wherein $\psi_0$ represents the angle of incidence to the eyeball which is known.

$$n_2^2 = \sin^2 \psi_0 [1 + \{\tan^2 \psi_0 (\cos^2 2\psi - \sin^2 2\psi \sin^2 \Delta)\}/(1 + \sin 2\psi \cos \Delta)^2]$$

Operation of the glucose concentration measuring system of this embodiment will be described, hereinbelow.

A laser beam is emitted from the semiconductor laser 10 and is collimated by the collimator lens 30. The major part of the collimated laser beam is reflected by the ND filer 60 toward the photodetector 76 and a part of the laser beam (intensity of Io') passes through the ND filter 60.

The collimated laser beam passing through the ND filter 60 is reflected by the mirror 31 at a predetermined angle and converted to linearly polarized light the λ/2 plate 15 and further converted to circularly polarized light by the λ/4 plate 18. The circularly polarized light is caused to impinge upon the interface between the cornea 210 and the aqueous humor 220 at a predetermined angle of incidence by the lens 19. At this time, since the circularly polarized light impinges upon the interface between the cornea 210 and the aqueous humor 220 at an angle, the circularly polarized light is in the form of an elliptically polarized light at the interface.

Further though the circularly polarized light is also reflected by other interfaces of the eyeball 200 only the backscattering light from the interface between the cornea 210 and the aqueous humor 220 can pass through the pin hole 35 by virtue of the confocal optical system.

The position of the analyzer 32 is adjusted so that the amount of light which passes through the pin hole 35 and is detected by the photodetector 75 is maximized, and the ellipticity ρ and the azimuth φ of elliptical polarization of the backscattering light are determined from the orientation of the analyzer 32 and the output of the photodetector 75 at the time the amount of light detected by the photodetector 75 is maximized.

The signal processing circuit 82 determines the refractive index $n_2$ of the aqueous humor 220 on the basis of the ellipticity ρ and the azimuth φ thus obtained and the angle of incidence of the circularly polarized light to the eyeball. Then the signal processing circuit 82 obtains the glucose concentration G in the aqueous humor 220 in the anterior chamber according to the correlation between the refractive index n of the aqueous humor 220 and the glucose concentration G therein. Then the display unit 90 shows the calculated glucose concentration G.

As can be understood from the description above, in the glucose concentration measuring system 100 of this embodiment, the glucose concentration in the aqueous humor can be noninvasively determined on the basis of the refractive index of the aqueous humor (refractive index at a portion near the interface between the cornea and the aqueous humor in the anterior chamber) which is determined on the basis of the state of the elliptically polarized backscattering light from the interface between the cornea and the aqueous humor spatially separated from other backscattering light by the confocal optical system. Further, the ND filter disposed on the optical path of the laser beam between the semiconductor laser and the eyeball reduce the intensity of the laser beam entering the eyeball not higher than a predetermined value of MPE, thereby making harmless the laser beam.

What is claimed is:

1. A method of measuring a glucose concentration in aqueous humor in an anterior chamber of an eyeball, comprising the steps of:

(a) projecting a semiconductor laser beam onto the eyeball which is placed at a predetermined position;

(b) detecting intensities of backscattered light generated by predetermined interfaces of the eyeball;

(c) measuring absorbance or refractive indexes of the aqueous humor in the anterior chamber of the eyeball based on the intensities of the backscattered light, wherein a single wavelength of the laser beam provides sufficient information for determining the intensity of the backscattered light which is reflected from the predetermined interfaces of the eyeball;

(d) determining the glucose concentration in the aqueous humor based on the absorbance or refractive indexes of the aqueous humor in the anterior chamber of the eyeball thus determined; and (e) controlling an intensity of the laser beam by disposing an extinction filter on an optical path of the laser beam between said semiconductor laser and the eyeball so that the intensity of the laser beam entering the eyeball is reduced not higher than a predetermined value of maximum permissible exposure.

2. The method as defined in claim 1, wherein the semiconductor laser emits a laser beam in a visible region or a near-infrared region at an intensity of several mW and the extinction filter is an ND filter whose optical density is in the range of 3 to 4 inclusive.

3. A method of measuring a glucose concentration in aqueous humor in an anterior chamber of an eyeball, comprising the steps of:

(a) projecting a semiconductor laser beam onto the eyeball which is placed in a predetermined position;

(b) detecting a state of elliptical polarization of backscattered light generated by a predetermined interface of the eyeball;

(c) measuring a refractive index of the aqueous humor in the anterior chamber of the eyeball based on the state of elliptical polarization of the backscattered light, wherein a single wavelength of the laser beam provides sufficient information for determining the elliptical polarization of the backscattered light which is reflected from the predetermined interfaces of the eyeball;

(d) determining the glucose concentration in the aqueous humor based on the refractive index of the aqueous humor in the anterior chamber thus determined; and (e) controlling an intensity of the laser beam by disposing an extinction filter on an optical path of the laser beam between the semiconductor laser and the eyeball so that the intensity of the laser beam entering the eyeball is reduced not higher than a predetermined value of maximum permissible exposure.

4. The method as defined in claim 3, wherein the semiconductor laser emits a laser beam in a visible region the extinction filter is an ND filter whose optical density is in the range of 3 to 4 inclusive.

5. A glucose concentration measuring system, comprising:

a semiconductor laser which projects a laser beam onto an eyeball placed at a predetermined position;

a detector which detects intensities of backscattered light generated by predetermined interfaces of the eyeball, wherein absorbance or refractive indexes of aqueous humor in an anterior chamber of the eyeball is measured based on the intensities of the backscattered light, wherein a single wavelength of the laser beam provides sufficient information for determining the intensities of the backscattered light which are reflected from the predetermined interfaces of the eyeball, and wherein the glucose concentration in the aqueous humor is determined based on the absorbance or refractive indexes of the aqueous humor in the anterior chamber thus determined; and an extinction filter disposed on an optical path of the laser beam between the semiconductor laser and the eyeball so that an intensity of the laser beam entering the eyeball is reduced not higher than a predetermined value of maximum permissible exposure.

6. The glucose concentration measuring system as defined in claim 5 wherein the semiconductor laser emits a laser beam in a visible region or a near-infrared region at an intensity of several mW and the extinction filter is an ND filter whose optical density is in the range of 3 to 4 inclusive.

7. A glucose concentration measuring system comprising:
a semiconductor laser which projects a laser beam onto an eyeball placed at a predetermined position;

a detector which detects a state of elliptical polarization of backscattered light generated by predetermined interfaces of an eyeball, wherein a refractive index of aqueous humor in an anterior chamber of the eyeball is determined based on the state of elliptical polarization of the backscattered light, wherein a single wavelength of the laser beam provides sufficient information for determining the elliptical polarization of the backscattered light which is reflected from the predetermined interfaces of the eyeball, and wherein the glucose concentration in the aqueous humor is determined based on the refractive index of the aqueous humor in the anterior chamber thus determined; and an extinction filter disposed on an optical path of the laser beam between the semiconductor laser and the eyeball so that an intensity of the laser beam entering the eyeball is reduced not higher than a predetermined value of maximum permissible exposure.

8. The glucose concentration measuring system as defined in claim 7 wherein the semiconductor laser emits a laser beam in a visible region or a near-infrared region at an intensity of several mW and the extinction filter is an ND filter whose optical density is in the range of 3 to 4 inclusive.

9. The method of measuring the glucose concentration in aqueous humor in the anterior chamber of the eyeball according to claim 1, wherein the step of detecting intensities of backscattered light is performed by measuring the intensities of a beat signal which beats at a frequency difference between the backscattered light and a reference light beam.

10. The method of measuring the glucose concentration in aqueous humor in the anterior chamber of the eyeball according to claim 1, wherein the wavelength of the semiconductor laser beam is modified so that the absorption properties of the aqueous humor are temperature independent.

11. The method of measuring the glucose concentration in aqueous humor in the anterior chamber of the eyeball according to claim 1, wherein correction coefficients are employed to correct the refractive indexes due to temperature variations in the eyeball.

12. The method of measuring the glucose concentration in aqueous humor in the anterior chamber of the eyeball according to claim 3, wherein the step of detecting intensities of backscattered light is performed by measuring the intensities of a beat signal which beats at a frequency difference between the backscattered light and a reference light beam.

13. The method of measuring the glucose concentration in aqueous humor in the anterior chamber of the eyeball according to claim 3, wherein the wavelength of the semiconductor laser beam is varied so that the absorption properties of the aqueous humor are temperature independent.

14. The method of measuring the glucose concentration in aqueous humor in the anterior chamber of the eyeball according to claim 3, wherein correction coefficients are employed to correct the refractive indexes due to temperature variations in the eyeball.

15. The glucose concentration measuring system according to claim 5, wherein a photodetector detects the intensities of backscattered light.

16. The glucose concentration measuring system according to claim 7, wherein a photodetector detects the intensities of backscattered light.

* * * * *